United States Patent
Sellman et al.

(10) Patent No.: US 10,759,849 B2
(45) Date of Patent: *Sep. 1, 2020

(54) **METHODS OF TREATING *S. AUREUS*-ASSOCIATED DISEASES**

(71) Applicant: MedImmune, LLC, Gaithersburg, MD (US)

(72) Inventors: Brett R. Sellman, Gaithersburg, MD (US); Christine Tkaczyk, Gaithersburg, MD (US); Melissa Hamilton, Gaithersburg, MD (US); Lei Hua, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/599,595

(22) Filed: Oct. 11, 2019

(65) Prior Publication Data

US 2020/0109191 A1    Apr. 9, 2020

Related U.S. Application Data

(63) Continuation of application No. 15/845,701, filed on Dec. 18, 2017, now Pat. No. 10,457,724, which is a continuation of application No. 14/440,749, filed as application No. PCT/US2013/068385 on Nov. 5, 2013, now Pat. No. 9,845,348.

(60) Provisional application No. 61/723,128, filed on Nov. 6, 2012.

(51) Int. Cl.
| | |
|---|---|
| *A61K 49/00* | (2006.01) |
| *A61K 39/085* | (2006.01) |
| *A61K 39/00* | (2006.01) |
| *C07K 16/12* | (2006.01) |

(52) U.S. Cl.
CPC ........ *C07K 16/1271* (2013.01); *A61K 39/085* (2013.01); *A61K 2039/505* (2013.01); *C07K 2317/52* (2013.01); *C07K 2317/565* (2013.01); *C07K 2317/76* (2013.01)

(58) Field of Classification Search
CPC ...... A61K 39/00; A61K 39/02; A61K 39/085; A61K 39/395; A61K 39/40
USPC ..... 424/9.1, 9.2, 130.1, 150.1, 184.1, 185.1, 424/234.1, 243.1
See application file for complete search history.

(56) References Cited

U.S. PATENT DOCUMENTS

| | | | |
|---|---|---|---|
| 9,527,905 B2 | 12/2016 | Sellman et al. | |
| 9,845,348 B2* | 12/2017 | Sellman | C07K 16/1271 |
| 9,879,070 B2 | 1/2018 | Sellman et al. | |
| 10,457,724 B2* | 10/2019 | Sellman | A61K 39/085 |
| 2012/0201829 A1 | 9/2012 | Rudolf et al. | |
| 2016/0257733 A1 | 9/2016 | Sellman et al. | |
| 2017/0129943 A1 | 5/2017 | Sellman et al. | |
| 2019/0002540 A1 | 1/2019 | Sellman et al. | |
| 2019/0016787 A1 | 1/2019 | Sellman et al. | |
| 2019/0077851 A1 | 3/2019 | Jafri et al. | |

FOREIGN PATENT DOCUMENTS

| | | |
|---|---|---|
| EP | 2284193 A1 | 2/2011 |
| WO | WO 2007/145689 A1 | 12/2007 |
| WO | WO 2009/029831 A1 | 5/2009 |
| WO | WO 2012/109167 A1 | 8/2012 |
| WO | WO 2012/109285 A2 | 8/2012 |
| WO | WO 2014/074540 A2 | 5/2014 |
| WO | WO 2015/196011 A1 | 12/2015 |
| WO | WO 2017/075188 A2 | 5/2017 |

OTHER PUBLICATIONS

Schubert, et at,"*Staphylococcus aureus* a-Toxin Triggers the Synthesis of B-Cell Lymphoma 3 by Human Platelets", Toxins, Jan. 2011, vol. 3, pp. 120-133.

McAdow, et al "Preventing *Staphylococcus aureus* Sepsis through the inhibition of its Agglutination in Blood", PLOS Pathogens, Oct. 2011, vol. 7, No. 10, pp. 1-12.

Parimon, et al., "*Staphylococcus aureus* a-Hemolysin Promotes Platelet-Neutrophil Aggregate Formation", The Journal of Infectious Diseases, Sep. 2013, vol. 208, pp. 761-770.

Adhikari, et al., "Novel Structurally Designed Vaccine for *S. Aureus* alpha-Hemolysin: Protection Against Bacteremia and Pneumonia", PLOS One, Jun. 2012, vol. 7, No. 6.

Kwak, et al., "The *Staphylococcus aureus* Alpha-Toxin Perturbs the Barrier Function in Caco-2 Epithelial Cell Monolayers by Altering Junctional Integrity", Infection and Immunity, May 2012, vol. 80, No. 5, pp. 1670-1680.

Ragle, et al, "Anti-Alpha-Hemolysin Monoclonal Antibodies Mediate Protection Against *Staphylococcus aureus* Pneumonia", Infection and Immunity, Jul. 2009, vol. 77, No. 7, pp. 2712-2718.

(Continued)

*Primary Examiner* — Rodney P Swartz
(74) *Attorney, Agent, or Firm* — Sterne, Kessler, Goldstein & Fox P.L.L.C.

(57) ABSTRACT

The present invention provides for methods of preventing and/or treating *S. aureus*-associated bacteremia and sepsis, and methods for preventing and/or treating *S. aureus*-associated pneumonia in immunocompromised patients using anti-*S. aureus* alpha-toxin (anti-AT) antibodies. Also provided are methods of reducing *S. aureus* bacterial load in the bloodstream or heart of a mammalian subject comprising administering to the subject an effective amount of an isolated anti-*S. aureus* alpha toxin (anti-AT) antibody or antigen-binding fragment thereof. Methods of reducing *S. aureus* bacterial agglutination and/or thromboembolic lesion formation in a mammalian subject comprising administering to the subject an effective amount of an isolated anti-*S. aureus* alpha toxin (anti-AT) antibody or antigen-binding fragment thereof, are also provided. Also provided are methods of preventing or reducing the severity of *S. aureus* associated pneumonia in an immunocompromised mammalian subject.

21 Claims, 7 Drawing Sheets

Figure 1:
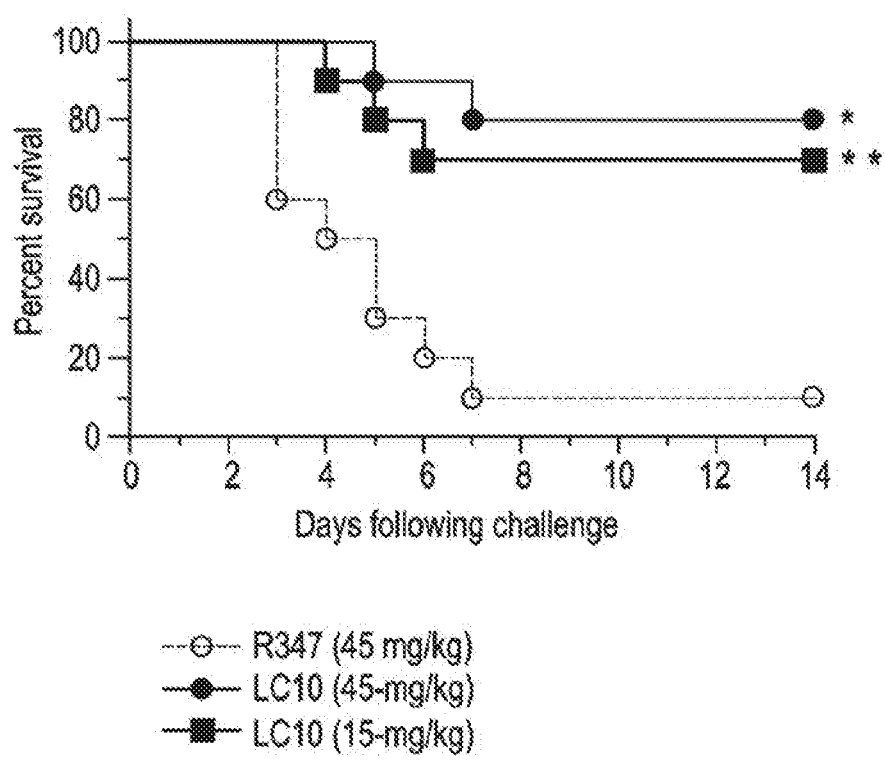

Specification includes a Sequence Listing.

(56) References Cited

OTHER PUBLICATIONS

Tkaczyk, et al, "Identification of Anti-Alpha Toxin Monoclonal Antibodies that Reduce the Severity of *Staphylococcus aureus* Dermonecrosis and Exhibit a Correlation Between Affinity an Potency", Clinical and Vaccine Immunology, Mar. 2012, vol. 19 No. 3, pp. 377-385.
International Search Report for PCT/US2013/068385 dated Feb. 20, 2014.
International Preliminary Report on Patentability for PCT/US2013/068385 dated May 12, 2015.
Written Opinion for International Application No. PCT/US2013/068385 dated Feb. 20, 2014.
European Supplementary Search Report for the Application No. EP 13853844 dated May 11, 2016.
Co-pending U.S. Appl. No. 16/521,223, inventors Tkaczyk, C. et al., filed Jul. 24, 2019 (Not Published).
Co-pending U.S. Appl. No. 16/596,388, inventors Tkaczyk, C. et al., filed Oct. 8, 2019 (Not Published).
Co-pending U.S. Appl. No. 16/596,445, inventors Tkaczyk, C. et al., filed Oct. 8, 2019 (Not Published).

\* cited by examiner

METHODS OF TREATING S. AUREUS-ASSOCIATED DISEASES

CROSS-REFERENCE TO RELATED APPLICATIONS

This application is continuation of U.S. application Ser. No. 15/845,701 (now U.S. Pat. No. 10,457,724), filed on Dec. 18, 2017, said U.S. application Ser. No. 15/845,701 is a continuation of U.S. application Ser. No. 14/440,749 (now U.S. Pat. No. 9,845,348), filed on May 5, 2015, said U.S. application Ser. No. 14/440,749 is a U.S. National Stage application of International Application No. PCT/US2013/068385, filed on Nov. 5, 2013, said International Application No. PCT/US2013/068385 claims benefit under 35 U.S.C. § 119(e) of U.S. Provisional Application No. 61/723,128, filed Nov. 6, 2012. Each of the above listed applications is incorporated by reference herein in its entirety for all purposes.

REFERENCE TO THE SEQUENCE LISTING

This application incorporates by reference a Sequence Listing submitted with this application as a text file entitled 2943_1070003_SeqListing_ST25.txt, created on Sep. 18, 2019, and having a size of 64,876.

BACKGROUND OF THE INVENTION

Field of the Invention

The present invention provides for methods of preventing and/or treating S. aureus-associated bacteremia and sepsis, and methods for preventing and/or treating S. aureus-associated pneumonia in immunocompromised patients using anti-S. aureus alpha-toxin (anti-AT) antibodies.

Background Art

Staphylococcus aureus (S. aureus) is a leading cause of mortality and morbidity worldwide, causing a diverse array of infections ranging from mild skin and soft-tissue infections to serious invasive diseases such endocarditis, osteomyelitis, and necrotizing pneumonia (Lowy F D, N Engl J Med, 339(8): 520-32 (1998); Klevens et al, JAMA 298(15): 1763-71 (2007). S. aureus is commonly classified as either methicillin resistant (MRSA) or methicillin sensitive (MSSA). Several reports have shown that S. aureus infections result in serious outcomes regardless of resistance status (Fowler et al, Arch Intern Med. 163(17):2066-72 (2003); de Kraker et al, PLoS Med. October; 8(10):e1001104 (2011).

Antibiotics are standard of care for treating S. aureus disease. Despite the introduction of new antibiotics against S. aureus, emergence of new resistance mechanisms requires new approaches to prevent or treat S. aureus diseases. Prior to the antibiotic era, passive administration of immune sera to infected patients was used clinically to treat bacterial infections (Keller and Stiehm, Clin Microbiol Rev 13(4): 602-14 (2000)). Today, similar methods are used to treat some toxin-mediated bacterial diseases (e.g., botulism, diphtheria, tetanus) (Keller and Stiehm, Clin Microbiol Rev 13(4):602-14 (2000); Arnon et al, N Engl. J. Med. 354: 462-471 (2006). S. aureus alpha toxin (AT) has been shown to be a key virulence determinant (amongst numerous other extracellular factors) in several S. aureus disease models (e.g., dermonecrosis, pneumonia, sepsis, endocarditis, and mastitis) by comparing S. aureus strains deficient for AT expression with isogenic wild-type parent strains (Bramley et al, Infect Immun. 57(8):2489-94 (1989); Bayer et al, Infect. Immun. 65: 4652-4660 (1997); Kernodle et al, Infect. Immun. 65: 179-184 (1997); Bubeck Wardenburg et al, Infect. Immun. 75(2):1040-4 (2007); Bubeck Wardenburg et al, J Exp Med. 205(2):287-94 (2008); Kobayashi et al, J Infect Dis. 204(6):937-41 (2011)).

AT is a cytolytic 33 kDa pore-forming toxin produced by 90% of S. aureus strains and is considered to be a major virulence factor. It is secreted as a monomer and binds the specific receptor ADAM-10 on target cell membranes (Wilke and Bubeck Wardenburg, PNAS 107(30):13473-8 (2010); Inoshima et al, Nat Med 17(10):1310-4 (2011). AT oligomerizes into a heptameric prepore and undergoes a conformational change resulting in transmembrane .beta.-barrel formation and subsequent cell lysis (Bhakdi and Tranum-Jensen, 1991; Song et al, 1996). Platelets, along with epithelial, endothelial, and immune cells (e.g., lymphocytes and macrophages), are susceptible to AT-lysis, suggesting the toxin has direct impact on tissue damage and immune evasion (Bhakdi and Tranum-Jensen, Microbiol Rev. 55 (4): 733-51 (1991); Ragle and Bubeck Wardenburg, Infect Immun. 77(7):2712-8 (2009); Tkaczyk et al, Clin Vaccine Immunol 19(3):377-85 (2012)). At sub-lytic concentrations, AT has also been demonstrated to exert significant cytotoxic effects (Grimminger et al, J Immunol. 159 (4):1909-16 (1997); Wilke and Bubeck Wardenburg, PNAS 107(30):13473-8 (2010); Inoshima et al, Nat Med 17(10): 1310-4 (2011)). AT binding and oligomerization on macrophage membranes activates the NLRP3 inflammasome that, along with other staphylococcal pathogen-associated molecular patterns (PAMPs), induces IL-1.beta. secretion and promotes cell death (Craven et al, PLoS One 4(10) (2009); Kebaier et al, J Infect Dis 205(5):807-17 (2012). Increased proinflammatory cytokine expression (e.g. IL-1.beta.) is a hallmark of acute lung injury (Goodman et al, Cytokine Growth Factor Rev. 14(6):523-35 (2003)).

AT also activates ADAM-10 mediated proteolysis of E-cadherin present in cell-cell adhesive contacts at sub-lytic concentrations, leading to a disruption in epithelium integrity and contributing to epithelial damage seen in pneumonia and skin and soft tissue infections (Inoshima et al, Nat Med 17(10):1310-4 (2011); Maretzky et al, PNAS 102(26): 9182-7 (2005); Inoshima et al, J Invest Dermatol. 132(5): 1513-6 (2012). AT exerts its cytotoxic effects through direct and indirect activities to create an environment conducive for bacterial growth and invasive disease. Consequently, targeted inhibition of AT could prevent or limit S. aureus-associated disease. This hypothesis is supported other studies which demonstrate reductions in S. aureus disease severity in murine infection models following active or passive immunization directed against AT (Menzies and Kemodle, Infect Immun 64(5):1839-41 (1996); Bubeck Wardenburg et al, J Exp Med. 205(2):287-94 (2008); Ragle and Bubeck Wardenburg, Infect Immun 77(7):2712-8 (2009); Kennedy et al, J Infect Dis. 202(7):1050-8 (2010); Tkaczyk et al, Clin Vaccine Immunol 19(3):377-85 (2012)).

An anti-AT antibody having an Fc variant region and its parent antibody LC10 are human, high-affinity, anti-AT mAbs (previously disclosed in U.S. Prov. Appl. No. 61/440, 581 and in Intl. Appl. No. PCT/US2012/024201 (published as WO2012/109205), the contents of each of which are herein incorporated by reference) and in Tkaczyk et al., Clinical and Vaccine Immunology, 19(3): 377 (2012).

Bacteremia and septic shock account for the majority of Staphylococcus aureus invasive disease (Klevens, et al, JAMA, 298(15): 1763-71 (2007). AT has been proposed to be an important virulence factor during *S. aureus* sepsis and to be responsible for endothelial damage during sepsis (Powers, et al, *J. Infect Dis.* 206(3):352-6 (2012). Interaction of AT with its receptor on endothelial cells allows the toxin to mediate vascular damage by direct cell lysis or activation of ADAM-10-mediated proteolysis of endothelial tight junctions (Id.). Both mechanisms would increase vascular permeability, a hallmark of bacterial sepsis.

While passive immunization with anti-AT monoclonal antibodies has been shown to result in a significant increase in survival in a murine model of staphylococcal pneumonia as described in U.S. Prov. Appl. No. 61/440,581 and in Intl. Appl. No. PCT/US2012/024201, it is not known whether anti-AT antibodies are effective in increasing survival in immunocompromised mammals having *S. aureus* associated diseases. This is a critical piece to understand as immunocompromised individuals, particularly those suffering from neutropenia, are at increased risk for *S. aureus* infections (Andrews and Sullivan, *Clin Microbiol Rev.* 16(4):597-621 (2003); Bouma et al., *Br J Haematol.* 151(4):312-26 (2010)).

The present invention provides, for the first time, a demonstration that anti-AT antibodies are effective in prophylaxis in sepsis and in immunocompromised pneumonia.

BRIEF SUMMARY OF THE INVENTION

Provided herein are methods for preventing or reducing the severity of *S. aureus*-associated sepsis in a mammalian subject comprising administering to the subject an effective amount of an isolated anti-*S. aureus* alpha toxin (anti-AT) antibody or antigen-binding fragment thereof. Also provided are methods of reducing *S. aureus* bacterial load in the bloodstream or heart of a mammalian subject comprising administering to the subject an effective amount of an isolated anti-*S. aureus* alpha toxin (anti-AT) antibody or antigen-binding fragment thereof. Methods of reducing *S. aureus* bacterial agglutination and/or thromboembolic lesion formation in a mammalian subject comprising administering to the subject an effective amount of an isolated anti-*S. aureus* alpha toxin (anti-AT) antibody or antigen-binding fragment thereof, are also provided. Also provided are methods of preventing or reducing the severity of *S. aureus*-associated pneumonia in an immunocompromised mammalian subject, comprising administering to the subject an effective amount of an isolated anti-*S. aureus* alpha toxin (anti-AT) antibody or antigen-binding fragment thereof.

In the various methods described herein, *S. aureus* bacterial load in the bloodstream or heart of the subject is suitably reduced, and in additional embodiments, *S. aureus* bacterial agglutination and/or thromboembolic lesion formation in the subject is reduced.

Suitably, the mammalian subject in the various methods described herein is human.

In the various methods, the isolated anti-AT antibody or antigen-binding fragment thereof is selected from the group consisting of Fv, Fab, Fab', and F(ab')2. In other embodiments, the antibody is a full-length antibody. In still further embodiments, the antibody comprises an Fc variant region.

In embodiments of the various methods described herein, the isolated antibody or antigen-binding fragment thereof immunospecifically binds to a *Staphylococcus aureus* alpha toxin polypeptide and includes:
(a) a VH CDR1 comprising the amino acid sequence of SEQ ID NO: 7, 10, 13 or 69;
(b) a VH CDR2 comprising the amino acid sequence of SEQ ID NO: 8, 11, 14, 17, 70 or 75;
(c) a VH CDR3 comprising the amino acid sequence of SEQ ID NO: 9, 12, 15, 18, 16, 65, 66, 67, 71, 72, 76 or 78;
(d) a VL CDR1 comprising the amino acid sequence of SEQ ID NO: 1 or 4;
(e) a VL CDR2 comprising the amino acid sequence of SEQ ID NO: 2, 5, 73 or 77; and
(f) a VL CDR3 comprising the amino acid sequence of SEQ ID NO: 3, 6, 64, 68 or 74.

In embodiments, the VH CDR1, VH CDR2, VH CDR3, VL CDR1, VL CDR2 and VL CDR3 for use in the various methods described herein correspond to the amino acid sequences of SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs: 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74

In additional embodiments, the isolated antibody or antigen-binding fragment thereof comprises a heavy chain variable domain having at least 90% identity to the amino acid sequence of SEQ ID NO: 20, 22, 24, 26, 28, 41, 43, 45, 47, 49, 51, 53, 55, 57, 79, 59, 61, or 62 and (iii) comprises a light chain variable domain having at least 90% identity to the amino acid sequence of SEQ ID NO: 19, 21, 23, 25, 27, 42, 44, 46, 48, 50, 52, 54, 56, 58, 60 or 63. Suitably, the isolated antibody or antigen-binding fragment thereof comprises a heavy chain variable domain of SEQ ID NO 20, 22, 24, 26, 28, 41, 43, 45, 47, 49, 51, 53, 55, 57, 79, 59, 61, or 62 and a light chain variable domain of SEQ ID NO: 19, 21, 23, 25, 27, 42, 44, 46, 48, 50, 52, 54, 56, 58, 60 or 63.

In additional embodiments of the various methods described herein, the VH and VL correspond to the amino acid sequences of SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

In still further embodiments of the various methods, the isolated antibody or antigen-binding fragment thereof comprises an anti-AT antibody having an Fc variant domain, wherein the antibody comprises a VH-IgG1-YTE corresponding to SEQ ID NO: 80 and/or a VL-Kappa corresponding to SEQ ID NO: 81.

BRIEF DESCRIPTIONS OF THE DRAWINGS

FIG. 1. LC10 prophylaxis improves survival in an IV lethal challenge model. Mice (10 per group) were passively immunized with LC10 (45 and 15 mg/kg), or an isotype control (R347, 45 mg/kg) 24-h prior to IV challenge with SF8300 ($3 \times 10^8$ cfu). Survival was monitored for 14 days. Data are representative of 4 independent experiments. Statistical significance was assessed with a log rank (Martel-Cox) test: *p-value=0.0005; **p-value=0.0043).

Figure 2:
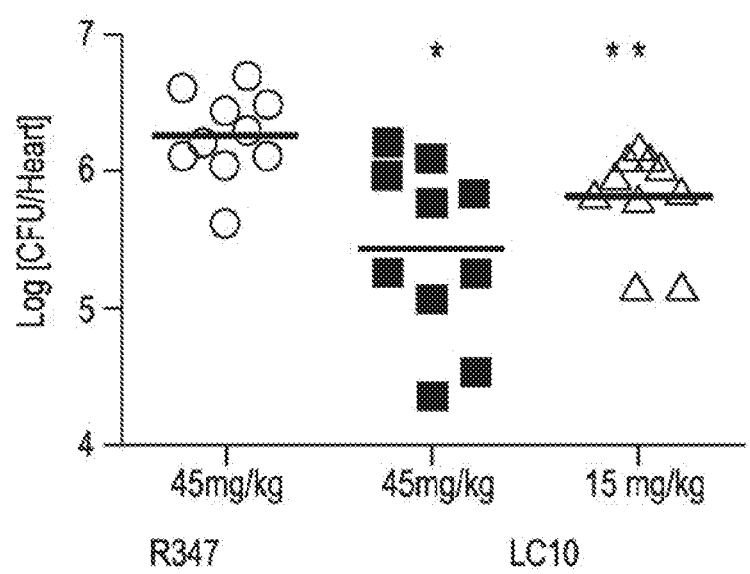

FIG. 2. LC10 prophylaxis reduces bacterial load in heart. Mice passively immunized with LC10 (45 and 15 mg/kg) or an isotype control (R347, 45 mg/kg) 24 hr prior to IV challenge with_SF8300 (2.98e8 cfu). Fourteen hours post-infection hearts from infected animals were collected and processed for CFU enumeration. Statistical analysis was performed with an unpaired 2-tailed Student's t-test: *p-value=0.0028; **p-value=0.0082).

Figure 3A:
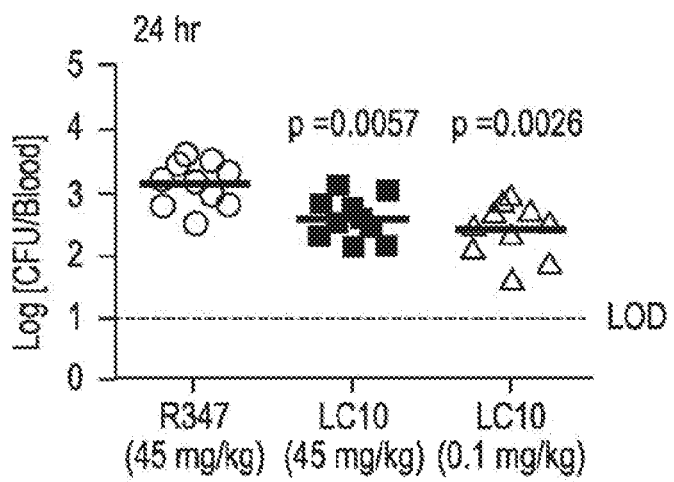
Figure 3B:
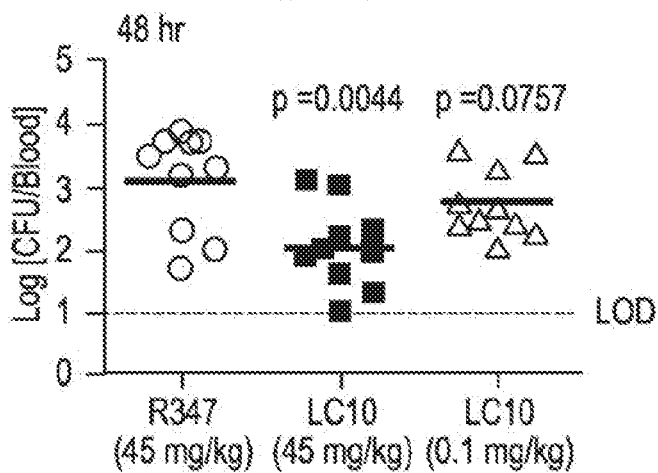
Figure 3C:
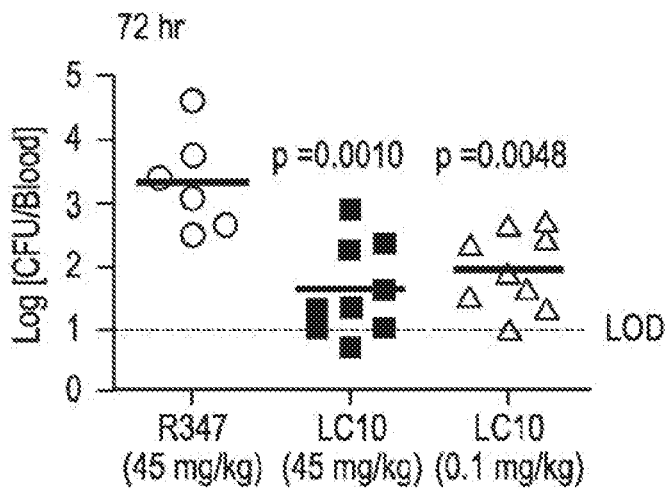

FIGS. 3A, 3B and 3C. LC10 prophylaxis reduces staphylococcal bacteremia. Mice were passively immunized with LC10 (45 and 15 mg/kg) or an isotype control (R347, 45 mg/kg) 24 h prior to IV challenge with SF8300 ($3 \times 10^8$ cfu). At 24 hours (FIG. 3A), 48 hours (FIG. 3B) and 72 hours (FIG. 3C) postinfection, blood was collected by cardiac puncture and plated for CFU enumeration. Statistical analysis was performed with a student t test. Data were considered statistically different vs R347 if *p-value<0.05.

Figure 4A:
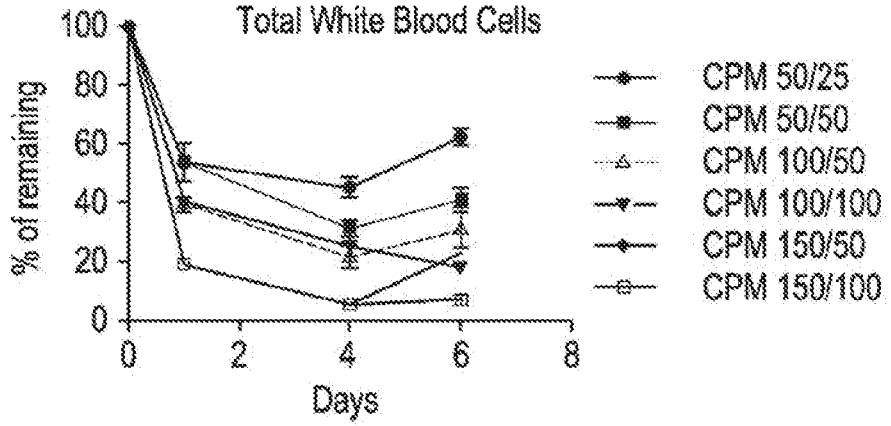
Figure 4B:
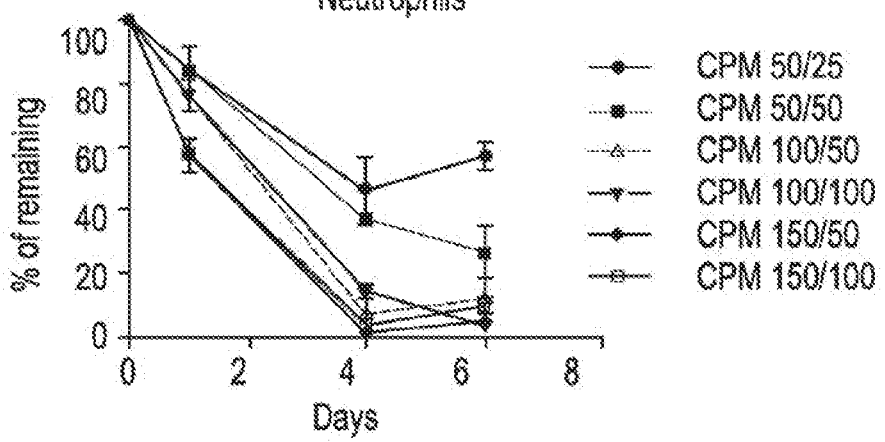
Figure 4C:
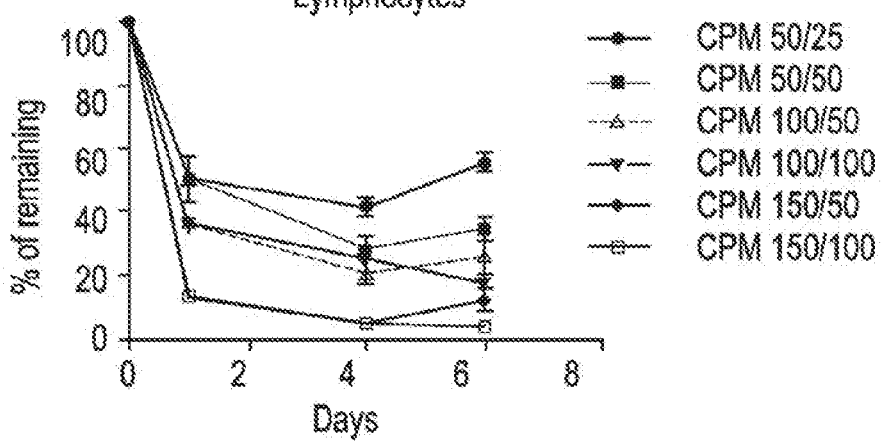

FIGS. 4A, 4B and 4C. Total and Differential White Blood Cell Counts. C57BL6/J mice were given 6 different doses of CPM (mg/kg) at Day 0 and Day 3. Blood samples of 5 mice per time point per group were taken on Days 0, 1, 4, and 6. Total white blood cells (FIG. 4A), neutrophils (FIG. 4B) and lymphocytes (FIG. 4C) were analyzed using a Sysmex automated hematology analyzer.

Figure 5:
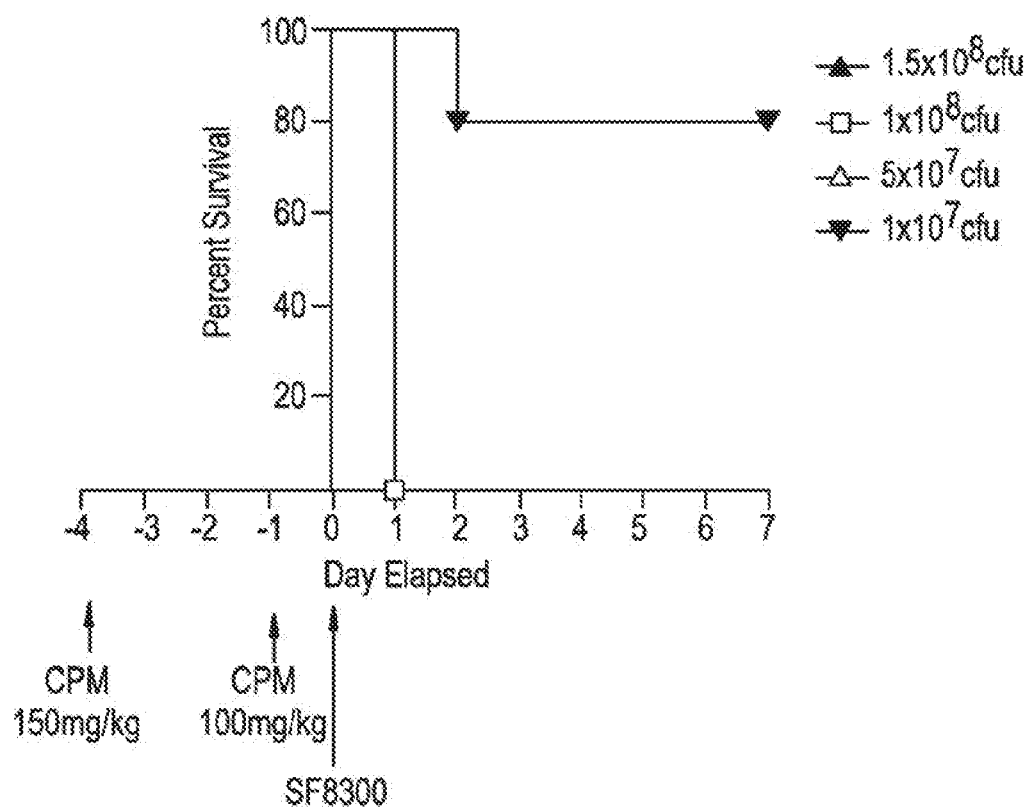

FIG. 5. Bacterial Dose Titration. Five immunocompromised mice were IN challenged with 50 µL log-phased bacterial suspension (dose ranging from $1 \times 10^7$ to $1.5 \times 10^8$ CFU) 24 hours after the second dose of CPM (Day 4). Animal survival was observed for a 7-day period.

Figure 6:
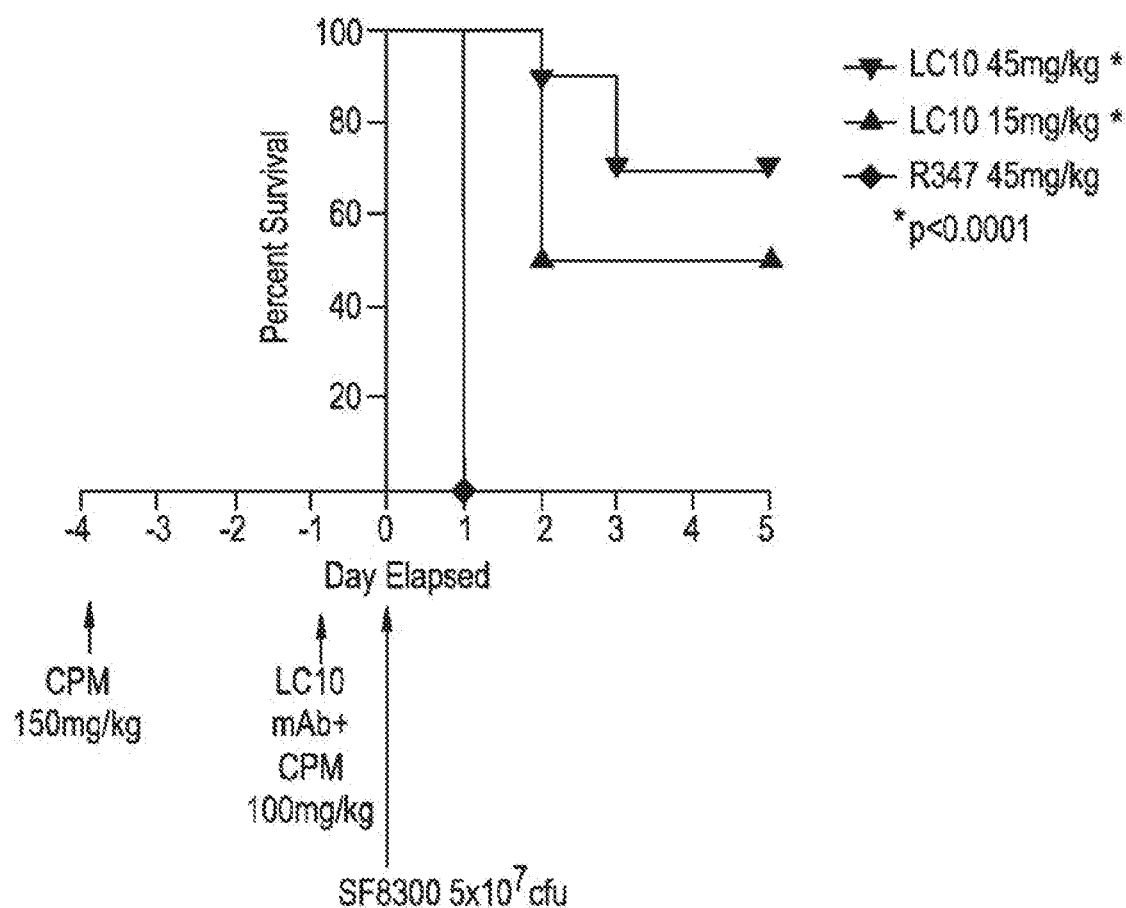

FIG. 6. LC10 Increases Survival in Immunocompromised Animals. CPM injected animals were administered LC10 (45 or 15 mg/kg) or R347 (45 mg/kg) 24 hr prior to IN infection with 50 µL of a bacterial suspension SF8300 ($5 \times 10^7$ CFU). Animal survival was monitored for 5 days. Statistical significance was determined using Log-rank test and * indicate statistical difference relative to animals treated with R347 (p<0.0001).

Figure 7:
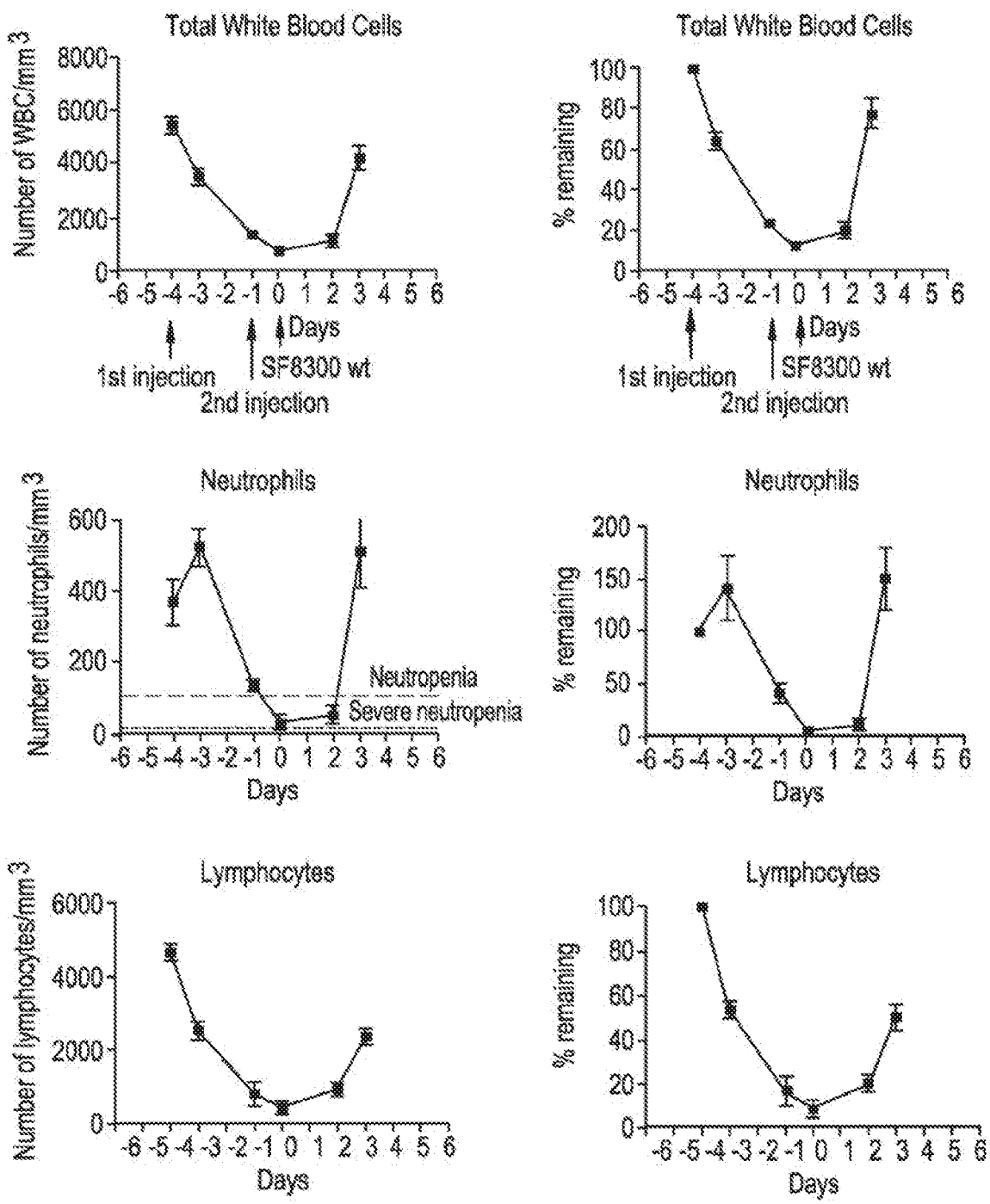

FIG. 7. Total and Differential White Blood Cell Counts. C57BL/6 mice were given 2 doses of CPM (150 mg/kg and 100 mg/kg) on Days −4 and −1, respectfully. Blood samples from 5 mice were collected on Days −4, −3, −1, 0, 2, and 3. Total and differential white blood cell counts (neutrophils, lymphocytes) were determined using a Sysmex automated hematology analyzer.

DETAILED DESCRIPTION OF THE INVENTION

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence.

As used herein, "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and antigen-binding fragments, as described herein. Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The terms "constant" and "variable" are used functionally.

The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia, et al., *J. Mol. Biol.* 186, 651-66 (1985); Novotny and Haber, *Proc. Natl. Acad. Sci. USA* 82, 4592-4596 (1985)). Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CH1, CH2, and CH3, and the heavy chains in IgM and IgE antibodies have four constant region domains, CH1, CH2, CH3, and CH4. Thus, heavy chains have one variable region and three or four constant regions. Immunoglobulin structure and function are reviewed, for example, in Harlow et al., Eds., Antibodies: A Laboratory Manual, Chapter 14, Cold Spring Harbor Laboratory, Cold Spring Harbor (1988).

References to "$V_H$" or a "VH" refer to the variable region of an immunoglobulin heavy chain, including an Fv, scFv, dsFv or Fab.

References to "$V_L$" or a "VL" refer to the variable region of an immunoglobulin light chain, including an Fv, scFv, dsFv, or Fab.

The term "antigen-binding fragment" refers to a portion of an intact antibody and refers to the antigenic determining variable regions of an intact antibody. Examples of antigen-binding fragments include, but are not limited to Fab, Fab', F(ab')2, Fv and single chain Fv fragments, linear antibodies, single chain antibodies, and multispecific antibodies formed from antigen-binding fragments.

The terms "single chain Fv" or "scFv" refers to an antibody in which the variable domains of the heavy chain and of the light chain of a traditional two chain antibody have been joined to form one chain. Terms include binding molecules which consist of one light chain variable domain ($V_L$) or portion thereof, and one heavy chain variable domain ($V_H$) or portion thereof, wherein each variable domain (or portion thereof) is derived from the same or different antibodies. scFv molecules typically comprise an scFv linker interposed between the $V_H$ domain and the $V_L$ domain. scFv molecules are known in the art and are described, e.g., in U.S. Pat. No. 5,892,019, Ho, et al., *Gene* 77:51-59 (1989); Bird, et al., *Science* 242:423-426 (1988); Pantoliano, et al., *Biochemistry* 30:10117-10125 (1991);

Milenic, et al., *Cancer Research* 51:6363-6371 (1991); Takkinen, et al., *Protein Engineering* 4:837-841 (1991), all of which are hereby incorporated by reference in their entireties.

Anti-*S. aureus* Alpha Toxin Antibodies and Antigen-Binding Fragments

An anti-*S. aureus* alpha toxin (also referred to as anti-*S. aureus* AT or anti-AT) antibody or antigen-binding fragment thereof, as utilized herein, immunospecifically binds to one or more epitopes specific to the alpha toxin protein, peptide, subunit, fragment, portion, oligomers or any combination thereof and generally do not specifically bind to other polypeptides. The term "oligomers" or "alpha toxin oligomers" refers to an association of alpha toxin monomers (e.g., 2 monomers, 3 monomers, 4 monomers, 5 monomers, 6 monomers or 7 monomers) to form a functional pore (e.g., 7 alpha toxin monomers). An epitope can comprise at least one antibody binding region that comprises at least one portion of the alpha toxin protein. The term "epitope" as used herein refers to a protein determinant capable of binding to an antibody. Epitopes generally include chemically active surface groupings of molecules such as amino acids and/or sugar side chains and generally have specific three dimensional structural characteristics, as well as specific chemical characteristics (e.g., charge, polarity, basic, acidic, hydrophobicity and the like). Conformational and non-conformational epitopes are distinguished in that the binding to the former but not the latter is lost in the presence of denaturing solvents. In some embodiments, the epitope recognized interferes with formation of the active heptamer (e.g., inhibits oligomerization of alpha toxin monomers into an active heptamer complex).

In certain embodiments, an epitope is comprised of at least a portion of the alpha toxin protein, which is involved in formation of an alpha toxin heptamer complex. A specified epitope can comprise any combination of at least one amino acid sequence of at least 3 amino acid residues to the entire specified portion of contiguous amino acids of the alpha toxin protein. In some embodiments, the epitope is at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, or at least 15 amino acid residues to the entire specified portion of contiguous amino acids of the alpha toxin protein. In certain other embodiments, the epitope comprises 1, 2, 3, 4, 5, 6, 7, 8, 9, 10, 11, 12, 13, 14 or 15 contiguous or non-contiguous amino acid residues. In further embodiments, the amino acid residues comprised within the epitope are involved in alpha toxin heptamer complex formation.

Thus, in specific embodiments, isolated/purified anti-alpha toxin antibodies and antigen-binding fragments immunospecifically bind to a molecule comprising the amino acid sequence according to SEQ ID NO: 39 and/or to a molecule comprising the amino acid sequence according to SEQ ID NO: 40. In certain embodiments, anti-alpha toxin antibodies and antigen-binding fragments also bind alpha toxin homologs or orthologs from different species, or to variants of the amino acid sequence of SEQ ID NO: 39, where the histidine at position 35 is replaced with leucine, or replaced with other amino acids corresponding to H35 mutations known to one of ordinary skill in the art.

Variable Regions

In certain embodiments, an anti-alpha toxin antibody or antigen-binding fragment is prepared from a parent antibody. In some embodiments, the anti-alpha toxin antibody or antigen-binding fragment is encompassed within the parent antibody. As used herein, the term "parent antibody" refers to an antibody that is encoded by an amino acid sequence used for the preparation of the variant or derivative, defined herein. A parent polypeptide may comprise a native antibody sequence (i.e., a naturally occurring, including a naturally occurring allelic variant) or an antibody sequence with pre-existing amino acid sequence modifications (such as other insertions, deletions and/or substitutions) of a naturally occurring sequence. A parent antibody may be a humanized antibody or a human antibody. In specific embodiments, anti-alpha toxin antibodies and antigen-binding fragments are variants of the parent antibody. As used herein, the term "variant" refers to an anti-alpha toxin antibody or antigen-binding fragment that differs in amino acid sequence from a "parent" anti-alpha toxin antibody or antigen-binding fragment amino acid sequence by virtue of addition, deletion and/or substitution of one or more amino acid residue(s) in the parent antibody sequence.

The antigen-binding portion of an antibody comprises one or more fragments of an antibody that retain the ability to specifically bind to an antigen (e.g., alpha toxin). It has been shown that the antigen-binding function of an antibody can be performed by fragments of a full-length antibody (i.e., antigen-binding fragments). Examples of "antigen-binding fragments" encompassed within the "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; and (vi) an isolated complementarity determining region (CDR). Although the two domains of the Fv fragment, VL and VH, often are coded for by separate genes, they can be joined, using recombinant methods, by a synthetic linker that enables them to be made as a single protein chain in which the VL and VH regions pair to form monovalent molecules (known as single chain Fv (scFv)). Such single chain antibodies also are encompassed within the terms "antibody and "antigen-binding fragment" of an antibody. These antigen-binding fragments can be obtained using known techniques, and the fragments can be screened for binding activity in the same manner as are intact antibodies. Antigen-binding fragments can be produced by recombinant DNA techniques, or by enzymatic or chemical cleavage of intact immunoglobulins.

The present anti-alpha toxin antibodies and antigen-binding fragments comprise at least one antigen binding domain. In some embodiments, an anti-alpha toxin antibody or antigen-binding fragment comprises a VH comprising the amino acid sequence of SEQ ID NO: 20, 22, 24, 26, 28, 41, 43, 45, 47, 49, 51, 53, 55, 57, 79, 59, 61, or 62. In certain embodiments, an anti-alpha toxin antibody or antigen-binding fragment comprises a VL comprising the amino acid sequence of SEQ ID NO: 19, 21, 23, 25, 27, 42, 44, 46, 48, 50, 52, 54, 56, 58, 60 or 63. In yet another embodiment, an anti-alpha toxin antibody or antigen-binding fragment comprises a VH comprising the amino acid sequence of SEQ ID NO: 20, 22, 24, 26, 28, 41, 43, 45, 47, 49, 51, 53, 55, 57, 79, 59, 61, or 62 and a VL comprising the amino acid sequence of SEQ ID NO: 19, 21, 23, 25, 27, 42, 44, 46, 48, 50, 52, 54, 56, 58, 60 or 63. See Table 7 for a representation of VH and VL sequences as presented herein which can be present in any combination to form an anti-alpha toxin antibody or antigen-binding fragment, or present in a combination to form a mAb of the invention. In some embodiments, the VH is selected from SEQ ID NO: 20, 22, 24, 26, 28, 41, 43, 45, 47, 49, 51, 53, 55, 57, 79, 59, 61, or 62. In various embodiments, the VL is selected from SEQ ID NO: 19, 21, 23, 25, 27, 42, 44, 46, 48, 50, 52, 54, 56, 58, 60 or 63. Certain VH and VL nucleotide sequences are presented in Table 8.

In some embodiments, the isolated antibody or antigen-binding fragment thereof comprises a VH and a VL, where the VH and VL have amino acid sequences represented by SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

Tables 1-7 provide heavy chain variable regions (VH), light chain variable regions (VL), and complementarity determining regions (CDRs) for certain embodiments of the antibodies and antigen-binding fragments presented herein. In certain embodiments, anti-alpha toxin antibodies and antigen-binding fragments comprise a VH and/or VL that has a given percent identify to at least one of the VH and/or VL sequences disclosed in Table 7. As used herein, the term "percent (%) sequence identity", also including "homology" is defined as the percentage of amino acid residues or nucleotides in a candidate sequence that are identical with the amino acid residues or nucleotides in the reference sequences, such as parent antibody sequence, after aligning the sequences and introducing gaps, if necessary, to achieve the maximum percent sequence identity, and not considering any conservative substitutions as part of the sequence identity. Optimal alignment of the sequences for comparison may be produced, besides manually, by means of local homology algorithms known in the art or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

In specific embodiments an antibody or antigen-binding fragment immunospecifically binds to alpha toxin and comprises a heavy chain variable domain comprising at least 90% identity to the amino acid sequence of SEQ ID NO: 20, 22, 24, 26, 28, 41, 43, 45, 47, 49, 51, 53, 55, 57, 79, 59, 61, or 62 and comprises a light chain variable domain comprising at least 90% identity to the amino acid sequence of SEQ ID NO: 19, 21, 23, 25, 27, 42, 44, 46, 48, 50, 52, 54, 56, 58, 60 or 63, where the antibody has the activity of inhibiting the binding of one or more alpha toxin monomers to each other (e.g., inhibits oligomerization).

Complementarily Determining Regions

While the variable domain (VH and VL) comprises the antigen-binding region, the variability is not evenly distributed through the variable domains of antibodies. It is concentrated in segments called Complementarity Determining Regions (CDRs), both in the light chain (VL or VK) and the heavy chain (VH) variable domains. The more highly conserved portions of the variable domains are called the framework regions (FR). The variable domains of native heavy and light chains each comprise four FR, largely adopting a β-sheet configuration, connected by three CDRs, which form loops connecting, and in some cases forming part of, the beta-sheet structure. The CDRs in each chain are held together in close proximity by the FR and, with the CDRs from the other chain, contribute to the formation of the antigen-binding site of antibodies (see, Kabat et al., supra). The three CDRs of the heavy chain are designated VH-CDR1, VH CDR2, and VH-CDR-3, and the three CDRs of the light chain are designated VL-CDR1, VL-CDR2, and V1-CDR3. The Kabat numbering system is used herein. As such, VH-CDR1 begins at approximately amino acid 31 (i.e., approximately 9 residues after the first cysteine residue), includes approximately 5-7 amino acids, and ends at the next serine residue. VH-CDR2 begins at the fifteenth residue after the end of CDR-H1, includes approximately 16-19 amino acids, and ends at the next glycine residue. VH-CDR3 begins at approximately the thirtieth amino acid residue after the end of VH-CDR2; includes approximately 13-15 amino acids; and ends at the sequence M-D-V. VL-CDR1 begins at approximately residue 24 (i.e., following a cysteine residue); includes approximately 10-15 residues; and ends with the sequence Y-V-S. VL-CDR2 begins at approximately the sixteenth residue after the end of VL-CDR1 and includes approximately 7 residues. VL-CDR3 begins at approximately the thirty-third residue after the end of VH-CDR2; includes approximately 7-11 residues and ends at the sequence T-I-L. Note that CDRs vary considerably from antibody to antibody (and by definition will not exhibit homology with the Kabat consensus sequences).

The present anti-alpha toxin antibodies and antigen-binding fragments comprise at least one antigen binding domain that includes at least one complementarity determining region (CDR1, CDR2 or CDR3). In some embodiments, an anti-alpha toxin antibody or antigen-binding fragment comprises a VH that includes at least one VH CDR (e.g., CDR-H1, CDR-H2 or CDR-H3). In certain embodiments, an anti-alpha toxin antibody or antigen-binding fragment comprises a VL that includes at least one VL CDR (e.g., CDR-L1, CDR-L2 or CDR-L3).

In some embodiments, the isolated antibody or antigen-binding fragment thereof that immunospecifically binds to a *Staphylococcus aureus* alpha toxin polypeptide includes, (a) a VH CDR1 comprising an amino acid sequence identical to, or comprising 1, 2, or 3 amino acid residue substitutions relative to SEQ ID NO: 7, 10, 13 or 69; (b) a VH CDR2 comprising an amino acid sequence identical to, or comprising 1, 2, or 3 amino acid residue substitutions relative to SEQ ID NO: 8, 11, 14, 17, 70 or 75; and (c) a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78.

In particular embodiments, the isolated antibody or antigen-binding fragment thereof comprises a VH CDR1, VH CDR2 and VH CDR3 comprising amino acid sequences identical to, or comprising 1, 2, or 3 amino acid residue substitutions in each CDR relative to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In some embodiments, the isolated antibody or antigen-binding fragment thereof that immunospecifically binds to a *Staphylococcus aureus* alpha toxin polypeptide includes, (a) a VL CDR1 comprising an amino acid sequence identical to, or comprising 1, 2, or 3 amino acid residue substitutions relative to SEQ ID NO: 1 or 4; (b) a VL CDR2 comprising an amino acid sequence identical to, or comprising 1, 2, or 3 amino acid residue substitutions relative to SEQ ID NO: 2, 5, 73 or 77; and (c) a VL CDR3 comprising an amino acid sequence identical to, or comprising 1, 2, or 3 amino acid residue substitutions relative to SEQ ID NO: 3, 6, 64, 68 or 74.

In particular embodiments, the isolated antibody or antigen-binding fragment thereof comprises a VL CDR1, VL CDR2 and VL CDR3 comprising amino acid sequences identical to, or comprising 1, 2, or 3 amino acid residue substitutions in each CDR relative to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In some embodiments, the isolated antibody or antigen-binding fragment thereof that immunospecifically binds to a Staphylococcus aureus alpha toxin polypeptide comprises a VH CDR1, VH CDR2, VH CDR3, VL CDR1, VL CDR2 and VL CDR3 comprising amino acid sequences identical to, or comprising 1, 2, or 3 amino acid residue substitutions in each CDR relative to: (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; (c) a VH CDR3 comprising the amino acid sequence of SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; and (f) a VL CDR3 comprising the amino acid sequence of SEQ ID NO: 3, 6, 64, 68 or 74.

In particular embodiments, the isolated antibody or antigen-binding fragment thereof comprises a VH CDR1, VH CDR2, VH CDR3, VL CDR1, VL CDR2, and VL CDR3 comprising amino acid sequences identical to, or comprising 1, 2, or 3 amino acid residue substitutions in each CDR relative to SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74, In some embodiments, provided is a composition that comprises an isolated antibody or antigen-binding fragment thereof that (i) includes a VH chain domain comprising three CDRs and a VL chain domain comprising three CDRs; and (ii) immunospecifically binds to a Staphylococcus aureus alpha toxin polypeptide, where the three CDRs of the VH chain domain include (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; and (c) a VH CDR3 comprising the amino acid sequence of SEQ ID NO: 9, 12, 15, 18, 16, 65, 66, 67, 71, 72, 76 or 78. In particular embodiments, the VH CDR1, VH CDR2 and VH CDR3 correspond to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

Also provided in certain embodiments is a composition that comprises an isolated antibody or antigen-binding fragment thereof that (i) includes a VH chain domain comprising three CDRs and a VL chain domain comprising three CDRs; and (ii) immunospecifically binds to a Staphylococcus aureus alpha toxin polypeptide, where the three CDRs of the VL chain domain include (a) a VL CDR1 comprising the amino acid sequence of SEQ ID NO: 1 or 4; (b) a VL CDR2 comprising the amino acid sequence of SEQ ID NO: 2, 5, 73, or 77; and (c) a VL CDR3 comprising the amino acid sequence of SEQ ID NO: 3, 6, 64, 68 or 74. In particular embodiments, the VL CDR1, VL CDR2 and VL CDR3 correspond to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In some embodiments, the isolated antibody or antigen-binding fragment thereof that immunospecifically binds to a Staphylococcus aureus alpha toxin polypeptide comprises a VH CDR1, VH CDR2, VH CDR3, VL CDR1, VL CDR2 and VL CDR3 comprising amino acid sequences identical to, or comprising 1, 2, or 3 amino acid residue substitutions in each CDR relative to: (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; (c) a VH CDR3 comprising the amino acid sequence of SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; and (f) a VL CDR3 comprising the amino acid sequence of SEQ ID NO: 3, 6, 64, 68 or 74.

In particular embodiments, the isolated antibody or antigen-binding fragment thereof comprises a VH CDR1, VH CDR2, VH CDR3, VL CDR1, VL CDR2, and VL CDR3 comprising amino acid sequences identical to, or comprising 1, 2, or 3 amino acid residue substitutions in each CDR relative to SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74, In some embodiments, provided is a composition that comprises an isolated antibody or antigen-binding fragment thereof that (i) includes a VH chain domain comprising three CDRs and a VL chain domain comprising three CDRs; and (ii) immunospecifically binds to a Staphylococcus aureus alpha toxin polypeptide, where the three CDRs of the VH chain domain include (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; and (c) a VH CDR3 comprising the amino acid sequence of SEQ ID NO: 9, 12, 15, 18, 16, 65, 66, 67, 71, 72, 76 or 78. In particular embodiments, the VH CDR1, VH CDR2 and VH CDR3 correspond to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

Provided also in some embodiments are compositions that include an isolated antibody or antigen-binding fragment thereof that (i) immunospecifically binds to a *Staphylococcus aureus* alpha toxin polypeptide, (ii) comprises a heavy chain variable domain comprising at least 90% identity to the amino acid sequence of SEQ ID NO: 20, 22, 24, 26, 28, 41, 43, 45, 47, 49, 51, 53, 55, 57, 79, 59, 61, or 62 and (iii) comprises a light chain variable domain comprising at least 90% identity to the amino acid sequence of SEQ ID NO: 19, 21, 23, 25, 27, 42, 44, 46, 48, 50, 52, 54, 56, 58, 60 or 63.

In some embodiments, the isolated antibody or antigen-binding fragment thereof includes a heavy chain variable domain of SEQ ID NO: 20, 22, 24, 26, 28, 41, 43, 45, 47, 49, 51, 53, 55, 57, 79, 59, 61, or 62 and a light chain variable domain of SEQ ID NO: 19, 21, 23, 25, 27, 42, 44, 46, 48, 50, 52, 54, 56, 58, 60 or 63.

In particular embodiments, the isolated antibody or antigen-binding fragment thereof comprises a VH and a VL, where the VH and VL are each identical to or each have at least 90%, 95% or 98% identity to the VH and VL amino acid sequences of SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

Variant Fc Regions

The present invention also includes binding members of the invention, and in particular the antibodies of the invention, that have modified IgG constant domains. Antibodies of the human IgG class, which have functional characteristics such as long half-life in serum and the ability to mediate various effector functions are used in certain embodiments of the invention (*Monoclonal Antibodies: Principles and Applications*, Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC as effector functions of the IgG class antibody, and it has been reported that among antibodies of the human IgG class, the IgG1 subclass has the highest ADCC activity and CDC activity in humans (*Chemical Immunology*, 65, 88 (1997)).

"Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998).

"Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.*, 23, 1098 (1993), *Immunology*, 86, 319 (1995), *Chemical Immunology*, 65, 88 (1997)) and that a sugar chain in the Cγ2 domain (*Chemical Immunology*, 65, 88 (1997)) is also important.

"Effector cells" are leukocytes that express one or more FcRs and perform effector functions. The cells express at least FcγRI, FcγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

The terms "Fc receptor" or "FcR" are used to describe a receptor that binds to the Fc region of an antibody. In one embodiment, the FcR is a native sequence human FcR. Moreover, in certain embodiments, the FcR is one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See, Daeron, Annu. Rev. Immunol., 15:203-234 (1997)). FcRs are reviewed in Ravetch and Kinet, Annu. Rev. Immunol, 9:457-92 (1991); Capel et al., Immunomethods, 4:25-34 (1994); and de Haas et al., J. Lab. Clin. Med. J, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., Immunol., 117:587 (1976) and Kim et al., J Immunol., 24:249 (1994)).

In certain embodiments, an anti-alpha toxin antibody or antigen-binding fragment comprises an altered Fc region (also referred to herein as "variant Fc region") in which one or more alterations have been made in the Fc region in order to change functional and/or pharmacokinetic properties of the antibodies. Such alterations may result in a decrease or increase of C1q binding and complement dependent cytotoxicity (CDC) or of FcgammaR binding, for IgG. The present technology encompasses the antibodies described herein with variant Fc regions where changes have been made to alter the effector function, providing a desired effect. Accordingly, in some embodiments an anti-alpha toxin antibody or antigen-binding fragment comprises a variant Fc region (i.e., Fc regions that have been altered as discussed below). Anti-alpha toxin antibodies and antigen-binding fragments herein comprising a variant Fc region are also referred to here as "Fc variant antibodies." As used herein native refers to the unmodified parental sequence and the antibody comprising a native Fc region is herein referred to as a "native Fc antibody". In some embodiments, the variant Fc region exhibits a similar level of inducing effector function as compared to the native Fc region. In certain embodiments, the variant Fc region exhibits a higher induction of effector function as compared to the native Fc. In certain embodiments, the variant Fc region exhibits lower induction of effector function as compared to the native Fc. Some specific embodiments of variant Fc regions are detailed herein. Methods for measuring effector function are known in the art.

Effector function of an antibody can be modified through changes in the Fc region, including but not limited to, amino acid substitutions, amino acid additions, amino acid deletions and changes in post translational modifications to Fc amino acids (e.g., glycosylation). Methods described below may be used to alter the effector function of an isolated antibody or antigen-binding fragment as described herein, resulting in an antibody or antigen-binding fragment having certain properties advantageous for prophylaxis or treatment of a particular Staphylococcal aureus-associated disease or condition.

In some embodiments an Fc variant antibody is prepared that has altered binding properties for an Fc ligand (e.g., an Fc receptor, C1q) relative to a native Fc antibody. Examples of binding properties include but are not limited to, binding specificity, equilibrium dissociation constant ($K_d$), dissociation and association rates (koff and kon respectively), binding affinity and/or avidity. It is known in the art that the equilibrium dissociation constant ($K_d$) is defined as koff/kon. In certain aspects, an antibody comprising an Fc variant region with a low $K_d$ may be more desirable to an antibody with a high $K_d$. However, in some instances the value of the kon or koff may be more relevant than the value of the $K_d$. It can be determined which kinetic parameter is more important for a given antibody application.

In some embodiments, Fc variant antibodies exhibit altered binding affinity for one or more Fc receptors including, but not limited to FcRn, FcgammaRI (CD64) including isoforms FcgammaRIA, FcgammaRIB, and FcgammaRIC; FcgammaRII (CD32 including isoforms FcgammaRIIA, FcgammaRIIB, and FcgammaRIIC); and FcgammaRIII (CD16, including isoforms FcgammaRIIIA and FcgammaRIIIB) as compared to an native Fc antibody.

In certain embodiments, an Fc variant antibody has enhanced binding to one or more Fc ligand relative to a native Fc antibody. In certain embodiments, the Fc variant antibody exhibits increased or decreased affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or is between 2 fold and 10 fold, or between 5 fold and 50 fold, or between 25 fold and 100 fold, or between 75 fold and 200 fold, or between 100 and 200 fold, more or less than a native Fc antibody. In various embodiments, Fc variant antibodies exhibit affinities for an Fc ligand that are at least 90%, at least 80%, at least 70%, at least 60%, at least 50%, at least 40%, at least 30%, at least 20%, at least 10%, or at least 5% more or less than an native Fc antibody. In certain embodiments, an Fc variant antibody has increased affinity for an Fc ligand. An Fc variant antibody may sometimes have decreased affinity for an Fc ligand.

In some embodiments, an Fc variant antibody has enhanced binding to the Fc receptor FcgammaRIIIA. In some embodiments, an Fc variant antibody has enhanced binding to the Fc receptor FcgammaRIIB. In certain embodiments, an Fc variant antibody has enhanced binding to both the Fc receptors FcgammaRIIIA and FcgammaRIIB. In certain embodiments, Fc variant antibodies that have enhanced binding to FcgammaRIIIA do not have a concomitant increase in binding the FcgammaRIIB receptor as compared to a native Fc antibody. In certain embodiments, an Fc variant antibody has reduced binding to the Fc receptor FcgammaRIIIA. An Fc variant antibody may sometimes have reduced binding to the Fc receptor FcgammaRIIB. In various embodiments, an Fc variant antibody exhibiting altered affinity for FcgammaRIIIA and/or FcgammaRIIB has enhanced binding to the Fc receptor FcRn. In some embodiments, an Fc variant antibody exhibiting altered affinity for FcgammaRIIIA and/or FcgammaRIIB has altered binding to C1q relative to a native Fc antibody.

In certain embodiments, Fc variant antibodies exhibit affinities for FcgammaRIIIA receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In various embodiments, Fc variant antibodies exhibit affinities for FcgammaRIIIA that are at least 90%, at least 80%, at least 70%, at least 60%, at least 50%, at least 40%, at least 30%, at least 20%, at least 10%, or at least 5% more or less than an native Fc antibody.

In certain embodiments, Fc variant antibodies exhibit affinities for FcgammaRIIB receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In certain embodiments, Fc variant antibodies exhibit affinities for FcgammaRIIB that are at least 90%, at least 80%, at least 70%, at least 60%, at least 50%, at least 40%, at least 30%, at least 20%, at least 10%, or at least 5% more or less than an native Fc antibody.

In some embodiments, Fc variant antibodies exhibit increased or decreased affinities to C1q relative to a native Fc antibody. In some embodiments, Fc variant antibodies exhibit affinities for C1q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In certain embodiments, Fc variant antibodies exhibit affinities for C1q that are at least 90%, at least 80%, at least 70%, at least 60%, at least 50%, at least 40%, at least 30%, at least 20%, at least 10%, or at least 5% more or less than an native Fc antibody. In various embodiments, an Fc variant antibody exhibiting altered affinity for Ciq has enhanced binding to the Fc receptor FcRn. In yet another specific embodiment, an Fc variant antibody exhibiting altered affinity for C1q has altered binding to FcgammaRIIIA and/or FcgammaRIIB relative to a native Fc antibody.

It is contemplated that Fc variant antibodies are characterized by in vitro functional assays for determining one or more FcgammaR mediated effector cell functions. In certain embodiments, Fc variant antibodies have similar binding properties and effector cell functions in in vivo models (such as those described and disclosed herein) as those in in vitro based assays. The present technology does not exclude Fc variant antibodies that do not exhibit the desired phenotype in in vitro based assays but do exhibit the desired phenotype in vivo.

The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

An increase in half-life allows for the reduction in amount of drug given to a patient as well as reducing the frequency of administration. An increase in half-life can also be beneficial, for example, for preventing a *Staphylococcal aureus*-associated disease or condition, and also for preventing a recurrence of infection that can often occur once a patient has been released from the hospital. To increase the serum half life of the antibody, one may incorporate a salvage receptor binding epitope into the antibody (especially an antigen-binding fragment) as known in the art. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Antibodies with increased half-lives may also be generated by modifying amino acid residues identified as involved in the interaction between the Fc and the FcRn receptor. In addition, the half-life of an anti-alpha toxin antibody or antigen-binding fragment may be increased by conjugation to PEG or Albumin by techniques widely utilized in the art. In some embodiments antibodies comprising Fc variant regions of an anti-alpha toxin antibody have an increased half-life of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to an antibody comprising a native Fc region. In some embodiments antibodies comprising Fc variant regions have an increased half-life of about 2 fold, about 3 fold, about 4 fold, about 5 fold, about 10 fold, about 20 fold, about 50 fold or more, or is between 2 fold and 10 fold, or between 5 fold and 25 fold, or between 15 fold and 50 fold, as compared to an antibody comprising a native Fc region.

In some embodiments, the technology presented herein provides Fc variants, where the Fc region comprises a modification (e.g., amino acid substitutions, amino acid insertions, amino acid deletions) at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non-naturally occurring amino acid residue at additional and/or alternative positions known in the art.

In a certain embodiments, provided herein is an Fc variant, where the Fc region comprises at least one substitution selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241 R. 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-naturally occurring amino acid residues known in the art.

In various embodiments, provided herein is an Fc variant antibody, where the Fc region comprises at least one modification (e.g., amino acid substitutions, amino acid insertions, amino acid deletions) at one or more positions selected from the group consisting of 234, 235 and 331. In some embodiments, the non-naturally occurring amino acids are selected from the group consisting of 234F, 235F, 235Y, and 331S. Provided herein is an Fc variant, where the Fc region comprises at least one non-naturally occurring amino acid at one or more positions selected from the group consisting of 239, 330 and 332. Some embodiments, the non-naturally occurring amino acids are selected from the group consisting of 239D, 330L and 332E.

In some embodiments, provided herein is an Fc variant antibody, where the Fc region comprises at least one non-naturally occurring amino acid at one or more positions selected from the group consisting of 252, 254, and 256. In certain embodiments, the non-naturally occurring amino acids are selected from the group consisting of 252Y, 254T and 256E, described in U.S. Pat. No. 7,083,784, the contents of which are herein incorporated by reference in its entirety.

In certain embodiments the effector functions elicited by IgG antibodies strongly depend on the carbohydrate moiety linked to the Fc region of the protein. Thus, glycosylation of the Fc region can be modified to increase or decrease effector function. Accordingly, in some embodiments the Fc regions of anti-alpha toxin antibodies and antigen-binding fragments provided herein comprise altered glycosylation of amino acid residues. In certain embodiments, the altered glycosylation of the amino acid residues results in lowered effector function. In certain embodiments, the altered glycosylation of the amino acid residues results in increased effector function. In some embodiments, the Fc region has reduced fucosylation. In certain embodiments, the Fc region is afucosylated.

In some embodiments, the Fc variants herein may be combined with other known Fc variants as known in the art. Other modifications and/or substitutions and/or additions and/or deletions of the Fc domain can be introduced. In particular embodiments, an anti-AT antibody of the invention having an Fc variant domain comprises a VH-IgG1-YTE corresponding to SEQ ID NO: 80 and/or a VL-Kappa corresponding to SEQ ID NO: 81.

Representative Sequences for Anti-*S. aureus* at Antibodies

TABLE 1

VL CDR sequences for mAbs 2A3.1, 10A7.5, 12B8.19 and 25E9.1

| SEQ ID NO: | Description | Sequence |
|---|---|---|
| SEQ ID NO: 1 | VL CDR1 | RASQSISSWLA |
| SEQ ID NO: 2 | VL CDR2 | KASSLES |
| SEQ ID NO: 3 | VL CDR3 | QQYNSYWT |

TABLE 2

VL CDR sequences for mAB 28F6.1

| SEQ ID NO: | Description | Sequence |
|---|---|---|
| SEQ ID NO: 4 | mAb 28F6.1 VL CDR1 | RASQGIRNDLG |
| SEQ ID NO: 5 | mAb 28F6.1 VL CDR2 | DASSLQS |
| SEQ ID NO: 6 | mAb 28F6.1 VL CDR3 | LQDYNYPWT |

TABLE 3

VH CDR sequences for mAb 2A3.1

| SEQ ID NO: | Description | Sequence |
|---|---|---|
| SEQ ID NO: 7 | VH CDR1 | SYDMH |
| SEQ ID NO: 8 | VH CDR2 | GIGTAGDTYYPGSVKG |
| SEQ ID NO: 9 | VH CDR3 | DNYSSTGGYYGMDV |

TABLE 4

VH CDR sequences for mAbs 10A7.5 and 12B8.19

| SEQ ID NO: | Description | Sequence |
|---|---|---|
| SEQ ID NO: 10 | VH CDR1 | RYDMH |
| SEQ ID NO: 11 | VH CDR2 | VIGTDGDTYYPGSVKG |
| SEQ ID NO: 12 | VH CDR3 | DRYSSSNHYNGMDV |

TABLE 5

VH CDR sequences for mAb 28F6.1

| SEQ ID NO: | Description | Sequence |
|---|---|---|
| SEQ ID NO: 13 | mAb 28F6.1 VH CDR1 | SYAMT |
| SEQ ID NO: 14 | mAb 28F6.1 VH CDR2 | VISGSGGSTYYADSVKG |
| SEQ ID NO: 15 | mAb 28F6.1 VH CDR3 | DGRQVEDYYYYGMDV |

TABLE 6

VH CDR sequences for mAb 25E9.1

| SEQ ID NO: | Description | Sequence |
|---|---|---|
| SEQ ID NO: 7 | mAb 25E9.1 VH CDR1 | SYDMH |
| SEQ ID NO: 17 | mAb 25E9.1 VH CDR2 | VIDTAGDTYYPGSVKG |
| SEQ ID NO: 18 | mAb 25E9.1 VH CDR3 | DRYSGNFHYNGMDV |

TABLE 7

VL and VH amino acid sequences for anti-alpha toxin mAbs

| Description | VH or VL sequence (with CDRs in bold) | CDR1 | CDR2 | CDR3 |
|---|---|---|---|---|
| mAb 2A3.1 VL | DIQMTQSPSTLSASVGDRVTIT CRASQSISSWLAWYQQKPGKA PKLLIYKASSLESGVPSRFSGSG SGTEFTLTISSLQPDDFATYYCQ QYNSYWTFGQGTKVEIK (SEQ ID NO: 19) | RASQSISS WLA (SEQ ID NO: 1) | KASSLES (SEQ ID NO: 2) | QQYNSYW T (SEQ ID NO: 3) |
| mAb 2A3.1 VH | EVQLVESGGGLVQPGGSLRLSC AASGFTFSSYDMHWVRQATG KGLEWVSGIGTAGDTYYPGS VKGRFTISRENAKNSLYLQLNS LRAGDTAVYFCARDNYSSTGG YYGMDVWGQGTTVTVSS (SEQ ID NO: 20) | SYDMH (SEQ ID NO: 7) | GIGTAGDT YYPGSVKG (SEQ ID NO: 8) | DNYSSTGG YYGMDV (SEQ ID NO: 9) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb 10A7.5 VL | DIQMTQSPSTLSASVGDRVTITCRASQSISSWLAWYQQKPGKA PKLLIYKASSLESGVPSRFSGSG SGTEFTLTISSLQPDDFATYYCQ QYNSYWTFGQGTKVEIK (SEQ ID NO: 21) | RASQSISS WLA (SEQ ID NO: 1) | KASSLES (SEQ ID NO: 2) | QQYNSYW T (SEQ ID NO: 3) |
| mAb 10A7.5 VH | EVQLVESGGGLVQPGGSLRLSC AASGFTFSRYDMHWVRQATG KGLEWVSVIGTDGDTYYPGSV KGRFIISRENAKNSLYLEMNSL RAGDTAVYYCARDRYSSSNHY NGMDVWGQGTTVTVSS (SEQ ID NO: 22) | RYDMH (SEQ ID NO: 10) | VIGTDGDT YYPGSVKG (SEQ ID NO: 11) | DRYSSSNH YNGMDV (SEQ ID NO: 12) |
| mAb 12B8.19 VL | DIQMTQSPSTLSASVGDRVTITCRASQSISSWLAWYQQKPGKA PKVLIYKASSLESGVPSRFSGS GSGTEFTLTISSLQPDDFATYYC QQYNSYWTFGQGTKVEIK (SEQ ID NO: 23) | RASQSISS WLA (SEQ ID NO: 1) | KASSLES (SEQ ID NO: 2) | QQYNSYW T (SEQ ID NO: 3) |
| mAb 12B8.19 VH | EVQLVESGGGLVQPGGSLRLSC AASGFTFSRYDMHWVRQATG KGLEWVSVIGTDGDTYYPGSV KGRFIISRENAKNSLYLEMNSL RAGDTAVYYCARDRYSSSNHY NGMDVWGQGTTVTVSS (SEQ ID NO: 24) | RYDMH (SEQ ID NO: 10) | VIGTDGDT YYPGSVKG (SEQ ID NO: 11) | DRYSSSNH YNGMDV (SEQ ID NO: 12) |
| mAb 28F6.1 VL | AIQMTQSPSSLSASVGDRVTITC RASQGIRNDLGWYQQKPGKA PKLLIYDASSLQSGVPSRFSGS SGTDFTLTISSLQPEDFATYYCL QDYNYPWTFGQGTKVEIK (SEQ ID NO: 25) | RASQGIRN DLG (SEQ ID NO: 4) | DASSLQS (SEQ ID NO: 5) | LQDYNYP WT (SEQ ID NO: 6) |
| mAb 28F6.1 VH | EVQLLESGGGLVQPGGSLRLSC AASGFTFSSYAMTWVRQAPGK GLEWVSVISGSGGSTYYADSV KGRFTVSRDNSKNTLYLQMNS LRAEDTAVYYCAKDGRQVED YYYYYGMDVWGQGTTVTVSS (SEQ ID NO: 26) | SYAMT (SEQ ID NO: 13) | VISGSGGST YYADSVK G (SEQ ID NO: 14) | DGRQVED YYYYYGM DV (SEQ ID NO: 15) |
| mAb 25E9.1 VL | DIQMTQSPSTLSASVGDRVTITCRASQSISSWLAWYQQKPGKA PKLLIYKASSLESGVPSRFSGSG SGTEFTLTISSLQPDDFATYYCQ QYNSYWTFGQGTKVEIK (SEQ ID NO: 27) | RASQSISS WLA (SEQ ID NO: 1) | KASSLES (SEQ ID NO: 2) | QQYNSYW T (SEQ ID NO: 3) |
| mAb 25E9.1 VH | EVQLVESGGGLVQPGGSLRLSC TASGFTFSSYDMHWVRQATGK GLEWVSVIDTAGDTYYPGSVK GRFTISRENAKNSLYLQMNSLR AGDTAVYYCVRDRYSGNFHY NGMDVWGQGTTVTVSS (SEQ ID NO: 28) | SYDMH (SEQ ID NO: 7) | SVIDTAGD TYYPGSVK G (SEQ ID NO: 17) | DRYSGNFH YNGMDV (SEQ ID NO: 18) |
| mAb QD20 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDRYSPTG HYMGMDVWGQGTTVTVSS (SEQ ID NO: 41) | SYDMH (SEQ ID NO: 7) | GIGTAGDT YYPGSVKG (SEQ ID NO: 8) | DRYSPTGH YMGMDV (SEQ ID NO: 16) |
| mAb QD20 VL | DIQMTQSPSTLSASVGDRVTITCRASQSISSWLAWYQQKPGKA PKLLIYKASSLESGVPSRFSGSG SGTEFTLTISSLQPDDFATYYCQ QYDTYWTFGQGTKVEIK (SEQ ID NO: 42) | RASQSISS WLA (SEQ ID NO: 1) | KASSLES (SEQ ID NO: 2) | QQYDTYW T (SEQ ID NO: 64) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb QD33 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDRYSRTG HYMGMDVWGQGTTVTVSS (SEQ ID NO: 43) | SYDMH (SEQ ID NO: 7) | GIGTAGDT YYPGSVKG (SEQ ID NO: 8) | DRYSRTGH YMGMDV (SEQ ID NO: 65) |
| mAb QD33 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 44) | RASQSISS WLA (SEQ ID NO: 1) | KASSLES (SEQ ID NO: 2) | QQYDTYW T (SEQ ID NO: 64) |
| mAb QD37 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDRYSRTG HYMGMSLWGQGTTVTVSS (SEQ ID NO: 45) | SYDMH (SEQ ID NO: 7) | GIGTAGDT YYPGSVKG (SEQ ID NO: 8) | DRYSRTGH YMGMSL (SEQ ID NO: 66) |
| mAb QD37 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 46) | RASQSISS WLA (SEQ ID NO: 1) | KASSLES (SEQ ID NO: 2) | QQYDTYW T (SEQ ID NO: 64) |
| mAb QD3 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDNYSRTG HYMGMDVWGQGTTVTVSS (SEQ ID NO: 47) | SYDMH (SEQ ID NO: 7) | GIGTAGDT YYPGSVKG (SEQ ID NO: 8) | DNYSRTGH YMGMDV (SEQ ID NO: 67) |
| mAb QD3 VL | DIQMTQSPSTLSASVGDRVTIT CRASQSISSWLAWYQQKPGKA PKLLIYKASSLESGVPSRFSGSG SGTEFTLTISSLQPDDFATYYCKQ QYADYWTFGQGTKVEIK (SEQ ID NO: 48) | RASQSISS WLA (SEQ ID NO: 1) | KASSLES (SEQ ID NO: 2) | KQYADYW T (SEQ ID NO: 68) |
| mAb QD4 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDNYSRTG HYMGMDVWGQGTTVTVSS (SEQ ID NO: 49) | SYDMH (SEQ ID NO: 7) | GIGTAGDT YYPGSVKG (SEQ ID NO: 8) | DNYSRTGH YMGMDV (SEQ ID NO: 67) |
| mAb QD4 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 50) | RASQSISS WLA (SEQ ID NO: 1) | KASSLES (SEQ ID NO: 2) | QQYDTYW T (SEQ ID NO: 64) |
| mAb QD23 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDRYSPTG HYMGMSLWGQGTTVTVSS (SEQ ID NO: 51) | SYDMH (SEQ ID NO: 7) | GIGTAGDT YYPGSVKG (SEQ ID NO: 8) | DRYSPTGH YMGMSL (SEQ ID NO: 78) |
| mAb QD23 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 52) | RASQSISS WLA (SEQ ID NO: 1) | KASSLES (SEQ ID NO: 2) | QQYDTYW T (SEQ ID NO: 64) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb QD32 VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDRYSRTG HYMGMDVWGQGTTVTVSS (SEQ ID NO: 53) | SYDMH (SEQ ID NO: 7) | GIGTAGDT YYPGSVKG (SEQ ID NO: 8) | DRYSRTGH YMGMDV NO: 65) |
| mAb QD32 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 54) | RASQSISS WLA (SEQ ID NO: 1) | KASSLES (SEQ ID NO: 2) | KQYADYW T (SEQ ID NO: 68) |
| mAb 2A3GL VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDNYSSTG GYYGMDVWGQGTTVTVSS (SEQ ID NO: 55) | SYDMH (SEQ ID NO: 7) | GIGTAGDT YYPGSVKG (SEQ ID NO: 8) | DNYSSTGG YYGMDV (SEQ ID NO: 9) |
| mAb 2A3GL VL | DIQMTQSPSTLSASVGDRVTIT CRASQSISSWLAWYQQKPGKA PKLLIYKASSLESGVPSRFSGSG SGTEFTLTISSLQPDDFATYYCQ QYNSYWTFGQGTKVEIK (SEQ ID NO: 56) | RASQSISS WLA (SEQ ID NO: 1) | KASSLES (SEQ ID NO: 2) | QQYNSYW T (SEQ ID NO: 3) |
| mAb LC10 VH | EVQLVESGGGLVQPGGSLRLSC AASGFTFSSHDMHWVRQATG KGLEWVSGIGTAGDTYYPDSV KGRFTISRENAKNSLYLQMNSL RAGDTAVYYCARDRYSPTGH YYGMDVWGQGTTVTVSS (SEQ ID NO: 57) | SHDMH (SEQ ID NO: 69) | GIGTAGDT YYPDSVKG (SEQ ID NO: 70) | DRYSPTGH YYGMDV (SEQ ID NO: 71) |
| mAb LC10 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 58) | RASQSISS WLA (SEQ ID NO: 1) | KASSLES (SEQ ID NO: 2) | KQYADYW T (SEQ ID NO: 68) |
| mAb TVES VH | EVQLVESGGGLVQPGGSLRLSC AASGFTFSSYDMHWVRQATG KGLEWVSGIGTAGDTYYPGS VKGRFTISRENAKNSLYLQMN SLRAGDTAVYYCARDNYSPTG GYYGMDVWGQGTTVTVSS (SEQ ID NO: 59) | SYDMH (SEQ ID NO: 7) | GIGTAGDT YYPGSVKG (SEQ ID NO: 8) | DNYSPTGG YYGMDV (SEQ ID NO: 72) |
| mAb TVES VL | DIQMTQSPSTLSASVGDRVTIT CRASQSISSWLAWYQQKPGKA PKLLIYKASSLKSGVPSRFSGS GSGTEFTLTISSLQPDDFATYYC QQYESYWTFGQGTKVEIK (SEQ ID NO: 60) | RASQSISS WLA (SEQ ID NO: 1) | KASSLKS (SEQ ID NO: 73) | QQYESYW T (SEQ ID NO: 74) |
| mAb 3H7KAD VH | EVQLVESGGGLVQPGGSLRLSC AASGFTFSSHDMHWVRQATG KGLEWVSGIGTRGDTYYPDSV KGRFTISRENAKNSLYLQMNSL RAGDTAVYYCARDRYSPTGH YYGMDVWGQGTTVTVSS (SEQ ID NO: 61) | SHDMH (SEQ ID NO: 69) | GIGTRGDT YYPDSVKG (SEQ ID NO: 75) | DRYSPTGH YYGMDV (SEQ ID NO: 71) |
| mAb 3H7KAD VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 58) | RASQSISS WLA (SEQ ID NO: 1) | KASSLES (SEQ ID NO: 2) | KQYADYW T (SEQ ID NO: 68) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb LC9 VH | EVQLVESGGGLVQPGGSLRLSC AASGFTFSSHDMHWVRQATG KGLEWVSGIGTRGDTYYPDSV KGRFTISRENAKNSLYLQMNSL RAGDTAVYYCARDKYSPTGH YYGMDVWGQGTTVTVSS (SEQ ID NO: 62) | SHDMH (SEQ ID NO: 69) | GIGTRGDT YYPDSVKG (SEQ ID NO: 75) | DKYSPTGH YYGMDV (SEQ ID NO: 76) |
| mAb LC9 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 58) | RASQSISS WLA (SEQ ID NO: 1) | KASSLES (SEQ ID NO: 2) | KQYADYW T (SEQ ID NO: 68) |
| mAb LC4 VH | EVQLVESGGGLVQPGGSLRLSC AASGFTFSSHDMHWVRQATG KGLEWVSGIGTRGDTYYPDSV KGRFTISRENAKNSLYLQMNSL RAGDTAVYYCARDKYSPTGH YYGMDVWGQGTTVTVSS (SEQ ID NO: 62) | SHDMH (SEQ ID NO: 69) | GIGTRGDT YYPDSVKG (SEQ ID NO: 75) | DKYSPTGH YYGMDV (SEQ ID NO: 76) |
| mAb LC4 VL | DIQMTQSPSTLSASVGDRVTIT CRASQSISSWLAWYQQKPGKA PKLLIYKASSLVKGVPSRFSGS GSGTEFTLTISSLQPDDFATYYC QQYESYWTFGQGTKVEIK (SEQ ID NO: 63) | RASQSISS WLA (SEQ ID NO: 1) | KASSLVK (SEQ ID NO: 77) | QQYESYW T (SEQ ID NO: 74) |
| mAb LC5 VH | EVQLVESGGGLVQPGGSLRLSC AASGFTFSSHDMHWVRQATG KGLEWVSGIGTAGDTYYPDSV KGRFTISRENAKNSLYLQMNSL RAGDTAVYYCARDRYSPTGH YYGMDVWGQGTTVTVSS (SEQ ID NO: 79) | SHDMH (SEQ ID NO: 69) | GIGTAGDT YYPDSVKG (SEQ ID NO: 70) | DRYSPTGH YYGMDV (SEQ ID NO: 71) |
| mAb LC5 VL | DIQMTQSPSTLSASVGDRVTIT CRASQSISSWLAWYQQKPGKA PKLLIYKASSLVKGVPSRFSGS GSGTEFTLTISSLQPDDFATYYC QQYESYWTFGQGTKVEIK (SEQ ID NO: 63) | RASQSISS WLA (SEQ ID NO: 1) | KASSLVK (SEQ ID NO: 77) | QQYESYW T (SEQ ID NO: 74) |

TABLE 8

VL and VH nucleotide sequences for anti-alpha toxin mAbs

| SEQ ID NO: | Description | Sequence |
|---|---|---|
| SEQ ID NO: 29 | mAb 2A3.1 VL nucleotide sequence | GACATCCAGATGACCCAGTCTCCTTCCAC CCTGTCTGCATCTGTAGGAGACAGAGTCA CCATCACTTGCCGGGCCAGTCAGAGTATT AGTAGCTGGTTGGCCTGGTATCAGCAGAA ACCAGGGAAAGCCCCTAAACTCCTGATCT ATAAGGCGTCTAGTTTAGAAAGTGGGGTC CCATCAAGGTTCAGCGGCAGTGGATCTGG GACAGAATTCACTCTCACCATCAGCAGCC TGCAGCCTGATGATTTTGCAACTTATTACT GCAACAGTATAATAGTTATTGGACGTTC GGCCAAGGGACCAAGGTGGAAATCAAA |
| SEQ ID NO: 30 | mAb 2A3.1 VH nucleotide sequence | GAGGTGCAGCTGGTGGAGTCTGGGGGAG GCTTGGTACAGCCTGGGGGGTCCCTGAGA CTCTCCTGTGCAGCCTCTGGATTCACCTTC AGTAGCTACGACATGCACTGGGTCCGCCA AGCTACAGGAAAAGGTCTGGAGTGGGTC TCAGGTATTGGCACTGCTGGTGACACATA TTATCCAGGCTCCGTGAAGGGCCGATTCA CCATCTCCAGAGAAAATGCCAAGAACTCC TTGTATCTTCAATTGAACAGCCTGAGAGC |

TABLE 8-continued

VL and VH nucleotide sequences for anti-alpha toxin mAbs

| SEQ ID NO: | Description | Sequence |
|---|---|---|
| | | CGGGGACACGGCTGTGTACTTCTGTGCAA GAGACAATTATAGCAGCACCGGGGGGTA CTACGGTATGGACGTCTGGGGCCAAGGG ACCACGGTCACCGTCTCCTCA |
| SEQ ID NO: 31 | mAb 10A7.5 VL nucleotide sequence | GACATCCAGATGACCCAGTCTCCTTCCAC CCTGTCTGCATCTGTAGGAGACAGAGTCA CCATCACTTGCCGGGCCAGTCAGAGTATT AGTAGCTGGTTGGCCTGGTATCAGCAGAA ACCAGGGAAAGCCCCTAAACTCCTGATCT ATAAGGCGTCTAGTTTAGAAAGTGGGGTC CCATCAAGGTTCAGCGGCAGTGGATCTGG GACAGAATTCACTCTCACCATCAGCAGCC TGCAGCCTGATGATTTTGCAACTTATTACT GCCAACAGTATAATAGTTATTGGACGTTC GGCCAAGGGACCAAGGTGGAAATCAAA |
| SEQ ID NO: 32 | mAb 10A7.5 VH nucleotide sequence | GAGGTGCAGCTGGTGGAGTCTGGGGGAG GCTTGGTACAGCCTGGGGGTCCCTGAGA CTCTCCTGTGCAGCCTCTGGATTCACCTTC AGTAGGTACGACATGCACTGGGTCCGCCA AGCTACAGGAAAAGGTCTGGAGTGGGTC TCAGTTATTGGTACTGATGGTGACACATA CTATCCAGGCTCCGTGAAGGGCCGATTCA TCATCTCCAGAGAAAATGCCAAGAACTCC TTGTATCTTGAAATGAACAGCCTGAGAGC CGGGGACACGGCTGTGTATTACTGTGCAA GAGATCGGTATAGCAGCTCGAACCACTAC AACGGTATGGACGTCTGGGGCCAAGGGA CCACGGTCACCGTCTCCTCA |
| SEQ ID NO: 33 | mAb 12B8.19 VL nucleotide sequence | GACATCCAGATGACCCAGTCTCCTTCCAC CCTGTCTGCATCTGTAGGAGACAGAGTCA CCATCACTTGCCGGGCCAGTCAGAGTATT AGTAGCTGGTTGGCCTGGTATCAGCAGAA ACCAGGGAAAGCCCCTAAGGTCCTGATCT ATAAGGCGTCTAGTTTAGAAAGTGGGGTC CCATCAAGGTTCAGCGGCAGTGGATCTGG GACAGAATTCACTCTCACCATCAGCAGCC TGCAGCCTGATGATTTTGCAACTTATTACT GCCAACAGTATAATAGTTATTGGACGTTC GGCCAAGGGACCAAGGTGGAAATCAAA |
| SEQ ID NO: 34 | mAb 12B8.19 VH nucleotide sequence | GAGGTGCAGCTGGTGGAGTCTGGGGGAG GCTTGGTACAGCCTGGGGGGTCCCTGAGA CTCTCCTGTGCAGCCTCTGGATTCACCTTC AGTAGGTACGACATGCACTGGGTCCGCCA AGCTACAGGAAAAGGTCTGGAGTGGGTC TCAGTTATTGGTACTGATGGTGACACATA CTATCCAGGCTCCGTGAAGGGCCGATTCA TCATCTCCAGAGAAAATGCCAAGAACTCC TTGTATCTTGAAATGAACAGCCTGAGAGC CGGGGACACGGCTGTGTATTACTGTGCAA GAGATCGGTATAGCAGCTCGAACCACTAC AACGGTATGGACGTCTGGGGCCAAGGGA CCACGGTCACCGTCTCCTCA |
| SEQ ID NO: 35 | mAb 28F6.1 VL nucleotide sequence | GCCATCCAGATGACCCAGTCTCCATCCTC CCTGTCTGCATCTGTAGGAGACAGAGTCA CCATCACTTGCCGGGCAAGTCAGGGCATT AGAAATGATTTAGGCTGGTATCAGCAGAA ACCAGGGAAAGCCCCTAAGCTCCTGATCT ATGATGCATCCAGTTTACAAAGTGGGGTC CCATCAAGGTTCAGCGGCAGTGGATCTGG CACAGATTTCACTCTCACCATCAGCAGCC TGCAGCCTGAAGATTTTGCAACTTATTAC TGTCTACAAGATTACAATTACCCGTGGAC GTTCGGCCAAGGGACCAAGGTGGAAATC AAA |
| SEQ ID NO: 36 | mAb 28F6.1 VH nucleotide sequence | GAGGTGCAGCTGTTGGAGTCTGGGGGAG GCTTGGTACAGCCTGGGGGGTCCCTGAGA CTCTCCTGTGCAGCCTCTGGATTCACCTTT AGCAGCTATGCCATGACCTGGGTCCGCCA GGCTCCAGGGAAGGGGCTGGAATGGGTC TCAGTTATTAGTGGTAGTGGTGGTAGCAC |

TABLE 8-continued

VL and VH nucleotide sequences for anti-alpha toxin mAbs

| SEQ ID NO: | Description | Sequence |
|---|---|---|
| | | ATACTACGCAGACTCCGTGAAGGGCCGGT<br>TCACCGTCTCCAGAGACAATTCCAAGAAC<br>ACGCTGTATCTGCAAATGAACAGCCTGAG<br>AGCCGAGGACACGGCCGTATATTACTGTG<br>CGAAAGATGGGAGGCAGGTCGAGGATTA<br>CTACTACTACTACGGTATGGACGTCTGGG<br>GCCAAGGGACCACGGTCACCGTCTCCTCA |
| SEQ ID NO: 37 | mAb 25E9.1 VL<br>nucleotide sequence | GACATCCAGATGACCCAGTCTCCTTCCAC<br>CCTGTCTGCATCTGTAGGAGACAGAGTCA<br>CCATCACTTGCCGGGCCAGTCAGAGTATT<br>AGTAGCTGGTTGGCCTGGTATCAGCAGAA<br>ACCAGGGAAAGCCCCTAAGCTCCTGATCT<br>ATAAGGCGTCTAGTTTAGAAAGTGGGGTC<br>CCATCAAGGTTCAGCGGCAGTGGATCTGG<br>GACAGAATTCACTCTCACCATCAGCAGCC<br>TGCAGCCTGATGATTTTGCAACTTATTACT<br>GCCAACAGTATAATAGTTATTGGACGTTC<br>GGCCAAGGGACCAAGGTGGAAATCAAA |
| SEQ ID NO: 38 | mAb 25E9.1 VH<br>nucleotide sequence | GAGGTGCAGCTGGTGGAGTCTGGGGGAG<br>GCTTGGTACAGCCTGGGGGGTCCCTGAGA<br>CTCTCCTGTACAGCCTCTGGATTCACCTTC<br>AGTAGTTACGACATGCACTGGGTCCGCCA<br>AGCTACAGGAAAAGGTCTGGAGTGGGTC<br>TCAGTTATTGATACTGCTGGTGACACATA<br>CTATCCAGGCTCCGTGAAGGGCCGATTCA<br>CCATCTCCAGAGAAAATGCCAAGAACTCC<br>TTGTATCTTCAAATGAACAGCCTGAGAGC<br>CGGGGACACGGCTGTGTATTACTGTGTAA<br>GAGATAGGTATAGTGGGAACTTCCACTAC<br>AACGGTATGGACGTCTGGGGCCAAGGGA<br>CCACGGTCACCGTCTCCTCA |

TABLE 9

Alpha Toxin VL and VH CDR summary table

| Description | SEQ ID NOs |
|---|---|
| VL CDR 1 | 1, 4 |
| VL CDR 2 | 2, 5, 73, 77 |
| VL CDR 3 | 3, 6, 64, 68, 74 |
| VH CDR 1 | 7, 10, 13, 69 |
| VH CDR 2 | 8, 11, 14, 17, 70, 75 |
| VH CDR 3 | 9, 12, 15, 18, 16, 65, 66, 67, 71, 72, 76, 78 |

TABLE 10

Alpha Toxin Amino Acid Sequences

| | |
|---|---|
| Staphylococcus aureus alpha toxin | adsdiniktgttdigsnttvktgdlvtydkengmhkkvfysfiddknhnkkllvirtkgtiagqyrvyseeganksgl<br>awpsafkvqlqlpdnevaqisdyyprnsidtkeymstltygfngnvtgddtgkiggliganvsightlkyvqpdfk<br>tilesptdkkvgwkvifnnmvnqnwgpydrdswnpvygnqlfmktrngsmkaadnfldpnkassllssgfsp<br>dfatvitmdrkaskqqtnidviyervrddyqlhwtstnwkgtntkdkwtdrsserykidwekeemtn (SEQ ID NO: 39) |
| S. aureus alpha toxin H35L mutant | adsdiniktgttdigsnttvktgdlvtydkengmlkkvfysfiddknhnkkllvirtkgtiagqyrvyseeganksgl<br>awpsafkvqlqlpdnevaqisdyyprnsidtkeymstltygfngnvtgddtgkiggliganvsightlkyvqpdfk<br>tilesptdkkvgwkvifnnmvnqnwgpydrdswnpvygnqlfmktrngsmkaadnfldpnkassllssgfsp<br>dfatvitmdrkaskqqtnidviyervrddyqlhwtstnwkgtntkdkwtdrsserykidwekeemtn (SEQ ID NO: 40) |

TABLE 11

VL and VH amino acid sequences for anti-alpha toxin mAbs having Fc variant region

| SEQ ID NO: | Description | Sequence |
|---|---|---|
| SEQ ID NO: 80 | LC 10-VH- IgG1-YTE: | EVQLVESGGGLVQPGGSLRLSCAASGFT<br>FSSHDMHWVRQATGKGLEWVSGIGTA |

TABLE 11-continued

VL and VH amino acid sequences for anti-alpha toxin mAbs having Fc variant region

| SEQ ID NO: | Description | Sequence |
|---|---|---|
| | | GDTYYPDSVKGRFTISRENAKNSLYLQ<br>MNSLRAGDTAVYYCARDRYSPTGHYY<br>GMDVWGQGTTVTVSS-<br>ASTKGPSVFPLAPSSKSTSGGTAALGCL<br>VKDYFPEPVTVSWNSGALTSGVHTFPA<br>VLQSSGLYSLSSVVTVPSSSLGTQTYICN<br>VNHKPSNTKVDKRVEPKSCDKTHTCPP<br>CPAPELLGGPSVFLFPPKPKDTLYITREP<br>EVTCVVVDVSHEDPEVKFNWYVDGVE<br>VHNAKTKPREEQYNSTYRVVSVLTVLH<br>QDWLNGKEYKCKVSNKALPAPIEKTIS<br>KAKGQPREPQVYTLPPSREEMTKNQVS<br>LTCLVKGFYPSDIAVEWESNGQPENNY<br>KTTPPVLDSDGSFFLYSKLTVDKSRWQ<br>QGNVFSCSVMHEALHNHYTQKSLSLSP<br>GK |
| SEQ ID NO: 81 | LC10 VL-Kappa | DIQMTQSPSTLSASVGDRVTITCRASQSI<br>SSWLAWYQQKPGKAPKLLIYKASSLES<br>GVPSRFSGSGSGTEFTLTISSLQPDDFAT<br>YYCKQYADYWTFGQGTKVEIK-<br>RTVAAPSVFIFPPSDEQLKSGTASVVCLL<br>NNFYPREAKVQWKVDNALQSGNSQES<br>VTEQDSKDSTYSLSSTLTLSKADYEKHK<br>VYACEVTHQGLSSPVTKSFNRGE |

Pharmaceutical Formulations Comprising Anti-At Antibodies and Antigen-Binding Fragments Thereof Also provided are pharmaceutical formulations comprising an anti-alpha toxin antibody or antigen-binding fragment thereof as described herein and a carrier. Such formulations can be readily administered in the various methods described throughout. In some embodiments, the formulation comprises a pharmaceutically acceptable carrier.

As used herein, the pharmaceutical formulations comprising an anti-alpha toxin antibody or antigen-binding fragment thereof are referred to as formulations of the technology. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co mingled with the antibodies and antigen-binding fragments described herein, and with each other, in a manner such that there is no interaction which would substantially impair the desired pharmaceutical efficacy.

Pharmaceutical compositions as described herein may be formulated for a particular dosage. Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound (i.e. antibody or antigen-binding fragment) calculated to produce the desired therapeutic effect in association with the required pharmaceutical carrier. The specification for the dosage unit forms are dictated by and directly dependent on (a) the unique characteristics of the anti-alpha toxin antibody or antigen-binding fragment and the particular therapeutic effect to be achieved, and (b) the limitations inherent in the art of compounding such an anti-alpha toxin antibody or antigen-binding fragment for the treatment of sensitivity in individuals.

Therapeutic compositions of the present technology can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient (i.e., antibody or antigen-binding fragment) which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Treatment of *S. aureus*-Associated Diseases

The present invention also provides methods of preventing and/or treating *S. aureus*-associated diseases and conditions, including for example bacteremia and sepsis using anti-*S. aureus* alpha-toxin (anti-AT) antibodies and antigen-binding fragments thereof. Also provided are methods for preventing and/or treating *S. aureus*-associated diseases and conditions, including for example, pneumonia in immunocompromised patients using anti-*S. aureus* alpha-toxin (anti-AT) antibodies and antigen-binding fragments thereof.

Any of the anti-AT antibodies or antigen-binding fragments thereof described throughout, as well as mutants, variants and derivatives of such antibodies, can be utilized in the various methods described herein. While exemplary anti-AT antibodies and antigen-binding fragments thereof are described herein for use in the various methods and in the Examples provided, it should be understood that any anti-AT antibody or antigen-binding fragment thereof known in the art, and particularly those described herein and disclosed in Published International Patent Application No. WO 2012/109285, the disclosure of which is incorporated by reference herein in its entirety, can be utilized in the various methods.

Also known as blood poisoning, bacteremia occurs when S. aureus bacteria enter a mammal's bloodstream, including humans. A persistent fever is one sign of bacteremia. The bacteria can travel to locations deep within the body, to produce infections affecting internal organs, such as brain, heart, lungs, bones and muscles, or surgically implanted devices, such as artificial joints or cardiac pacemakers. One hallmark of S. aureus sepsis is bacterial agglutination and thromboembolic lesion formation which is measured as bacterial colony forming units (CFU) in the heart (McAdow et al, 2011).

In embodiments, methods are provided for preventing S. aureus-associated sepsis in a mammalian subject or reducing the severity of S. aureus-associated sepsis in a mammalian subject. Such methods suitably comprise administering to the subject an effective amount of an isolated anti-S. aureus alpha toxin (anti-AT) antibody or antigen-binding fragment thereof, including isolated anti-S. aureus alpha toxin (anti-AT) antibodies or antigen-binding fragments described herein or otherwise known in the art.

Methods of preventing S. aureus-associated sepsis in a mammalian subject suitably comprise administering an effective amount of an isolated anti-AT antibody or antigen-binding fragment thereof to the subject prior to an infection event. As used herein, "infection event" refers to an event during which the subject is, or could be, exposed to S. aureus infection. Exemplary infection events include, but are not limited to, surgery on any part of the body, including head, mouth, hands, arms, legs, trunk, internal organs (e.g., heart, brain, bowels, kidneys, stomach, lungs, liver, spleen, pancreas, etc.), bones, skin. Surgery provides conditions, such as open surgical wounds and organs, which can readily be infected with S. aureus. Additional infection events include trauma to any part of the body that provides open wounds or otherwise access to the bloodstream via which S. aureus infection could enter the body. Additional infection events include blood transfusions, injections of medications or illegal or legal drugs, needle pricks, tattoo needles, insertion and maintenance of intravenous (IV) lines, insertion and maintenance of surgical drains, and sites of skin breakdown e.g., bedsores (decubitus ulcers).

In embodiments where the methods provide prevention of S. aureus-associated sepsis, the anti-AT antibody or antigen-binding fragment thereof is suitably administered at least 1 hour prior to an infection event. For example, at least 1 hour prior to surgery (the infection event). Suitably, the anti-AT antibody or antigen-binding fragment thereof is administered at least 6 hours, at least 12 hours, at least 18 hours, at least 24 hours, at least 30 hours, at least 36 hours, at least 42 hours, at least 48 hours, or longer, prior to the infection event. In embodiments, the anti-AT antibody or antigen-binding fragment thereof is suitably administered about 6 hours to about 36 hours, about 6 hours to about 36 hours, about 12 hours to about 36 hours, about 12 hours to about 24 hours, about 24 hours to about 36 hours, about 20 hours to about 30 hours, about 20 hours to about 28 hours, about 22 hours to about 26 hours, or about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, or about 30 hours, or about 31 hours, or about 32 hours, or about 33 hours, or about 34 hours, or about 35 hours, or about 36 hours, prior to the infection event.

As used herein "prevention" of S. aureus-associated sepsis refers to reducing the risk of a subject acquiring S. aureus-associated sepsis at the time of the infection event. Suitably, the risk of a subject acquiring S. aureus-associated sepsis is reduced by at least 30% as compared to a subject that has not been administered an anti-AT antibody or antigen-binding fragment prior to the infection event. More suitably the risk is reduced by at least 40%, at least 50%, at least 60%, at least 70%, at least 80%, at least 90% or the risk is completely eliminated as compared to a subject that has not been administered an anti-AT antibody or antigen-binding fragment prior to the infection event.

In methods for reducing the severity of S. aureus-associated sepsis in a mammalian subject, such methods suitably comprise administering an effective amount of an isolated anti-S. aureus alpha toxin (anti-AT) antibody or antigen-binding fragment thereof to a subject that is exhibiting symptoms of S. aureus-associated sepsis. Such symptoms can include, for example, chills, confusion or delirium, fever or low body temperature (hypothermia), light-headedness due to low blood pressure, rapid heartbeat, shaking, skin rash and warm skin.

As used herein "reducing the severity" as it is used with reference to sepsis refers to reducing the symptoms that a subject that has acquired S. aureus-associated sepsis is exhibiting. Suitably, the symptoms are reduced by at least 30% as compared to the symptoms that a subject that also has acquired S. aureus-associated sepsis is exhibiting, but the subject has not been administered an anti-AT antibody or antigen-binding fragment thereof. More suitably the symptoms are is reduced by at least 40%, at least 50%, at least 60%, at least 70%, at least 80%, at least 90% or the symptoms are completely eliminated (i.e., the subject is cured of the infection and the sepsis) as compared to a subject that has not been administered an anti-AT antibody or antigen-binding fragment thereof prior to the infection event.

As used herein, the terms "treat," "treating" or "treatment" can refer to therapeutic treatment and prophylactic or preventative measures, wherein the object is to prevent or slow down (lessen) an undesired physiological change or disorder, such as the progression of the disease. Beneficial or desired clinical results include, but are not limited to, alleviation of symptoms, diminishment of extent of disease, stabilized (i.e., not worsening) state of disease, delay or slowing of disease progression, amelioration or palliation of the disease state. "Treatment" can also mean prolonging survival as compared to expected survival if not receiving treatment. Those in need of treatment include those already with the condition or disorder as well as those prone to have the condition or disorder or those in which the condition or disorder is to be prevented.

Suitably subjects that can be administered the anti-AT antibodies or antigen-binding fragments thereof in the various methods described herein are mammals, such as for example, humans, dogs, cats, primates, cattle, sheep, horses, pigs, etc.

An antibody or antigen-binding fragment thereof described herein can be administered at a suitable dosage and dosage regimen, and such dosage and dosage regimen can depend on the disease or condition. An "effective dosage" can be identified by determining whether a dosage and dosage regimen gives rise to a therapeutic effect or therapeutic end-point (e.g., prevention). Dosing of the antibody or antigen-binding fragment thereof can be provided in a single administration, or over multiple administrations spaced according to desired effects and other clinical considerations.

Exemplary methods by which the anti-AT antibody or antigen-binding fragment thereof can be administered to the subject in any of the various methods described herein include, but are not limited to, intravenous (IV), intratumoral (IT), intralesional (IL), aerosal, percutaneous, endoscopic, topical, intramuscular (IM), intradermal (ID), intraocular (IO), intraperitoneal (IP), transdermal (TD), intranasal (IN), intracereberal (IC), intraorgan (e.g. intrahepatic), slow release implant, or subcutaneous administration, or via administration using an osmotic or mechanical pump.

In further embodiments, methods of reducing S. aureus bacterial load in the bloodstream or heart of a mammalian subject are provided. Such methods suitably comprise administering to the subject an effective amount of an isolated anti-S. aureus alpha toxin (anti-AT) antibody or antigen-binding fragment thereof.

Bacterial load in the bloodstream or heart of a mammalian subject is suitably measured via methods known in the art to determine the amount of bacteria, suitably S. aureus bacterial colonies, in the bloodstream or heart. For example, bacterial load is suitably measured by plating a sample from an organism onto an agar plate, incubating the plate, and then quantifying the number of colony forming units (CFU) on the plate. Such methods are well known in the art. Additional suitable methods for determining bacterial load can also be utilized. The collected sample is suitably from a blood sample from an organism taken generally, or specifically, from a particular organ.

Suitably, the bacterial load (i.e., the amount of bacteria as measured by colony forming units) of a subject infected with S. aureus is reduced by at least 30% in subjects treated with anti-AT antibodies or antigen-binding fragments thereof, as compared to subjects that also have been infected with S. aureus, but the subject has not been administered an anti-AT antibody or antigen-binding fragment thereof. More suitably the amount of bacteria is reduced by at least 40%, at least 50%, at least 60%, at least 70%, at least 80%, at least 90% or the bacterial load is completely eliminated as compared to a subject that has not been administered an anti-AT antibody or antigen-binding fragment.

Suitably, the anti-AT antibodies or antibody antigen-binding fragments thereof are administered as soon as possible after diagnosis of infection with S. aureus, e.g., within hours or days. The duration and amount of anti-AT antibodies or antigen-binding fragments to be administered are readily determined by those of ordinary skill in the art.

Also provided are methods of reducing S. aureus bacterial agglutination and/or thromboembolic lesion formation in a mammalian subject. Such methods suitably comprise administering to said subject an effective amount of an isolated anti-S. aureus alpha toxin (anti-AT) antibody or antigen-binding fragment thereof, including anti-S. aureus alpha toxin (anti-AT) antibodies or antigen-binding fragments thereof described herein or otherwise known in the art.

As described herein, methods of reducing S. aureus bacterial agglutination refer to lowering the amount of clumping between S. aureus bacteria when in contact with blood and/or in an organ. Exemplary methods of measuring bacterial agglutination are known in the art, including for example, as described in McAdow et al., PLos Pathogens 7:e1002307 (2011), the disclosure of which is incorporated by reference herein in its entirety. Suitably, the methods provided herein also lower thromboembolic lesion formation in the bloodstream and/or organs of a subject. Methods of measuring thromboembolic lesion formation are known in the art and include, for example, magnetic resonance imaging (MRI), computed tomography (CT) or computed axial tomography (CAT) scan, or other suitable imaging methods.

Methods of reducing *S. aureus* bacterial agglutination and/or thromboembolic lesion formation in a mammalian subject suitably result in a reduction of bacterial agglutination and/or thromboembolic lesion formation by at least 30% in subjects treated with anti-AT antibodies or antigen-binding fragments thereof, as compared to subjects that also have been infected with *S. aureus*, but the subject has not been administered an anti-AT antibody or antigen-binding fragment thereof. More suitably, the bacterial agglutination and/or thromboembolic lesion formation is reduced by at least 40%, at least 50%, at least 60%, at least 70%, at least 80%, at least 90% or bacterial agglutination and/or thromboembolic lesion formation is completely eliminated as compared to a subject that has not been administered an anti-AT antibody or antigen-binding fragment thereof.

Suitably, the methods of preventing *S. aureus*-associated sepsis in a mammalian subject or reducing the severity of *S. aureus*-associated sepsis in a mammalian subject also result in reduction of bacterial load in the bloodstream or heart of the subject. In other embodiments, the methods of preventing *S. aureus*-associated sepsis in a mammalian subject or reducing the severity of *S. aureus*-associated sepsis in a mammalian subject also result in reduction of bacterial agglutination and/or thromboembolic lesion formation in the subject.

In additional embodiments, methods of preventing or reducing the severity of *S. aureus*-associated pneumonia in an immunocompromised mammalian subject are provided. Such methods suitably comprise administering to the subject an effective amount of an isolated anti-*S. aureus* alpha toxin (anti-AT) antibody or antigen-binding fragment thereof.

As described herein, it has been surprisingly found that immunocompromised mammalian subjects can be administered anti-AT antibodies or antigen-binding fragments thereof so as to either prevent *S. aureus*-associated pneumonia, or to reduce the severity of *S. aureus*-associated pneumonia in subjects that have already contracted pneumonia.

As used herein "immunocompromised" refers to mammalian subjects that are incapable of developing a normal immune response, and generally such subjects are suffering from neutropenia, which refers to an abnormally low number of neutrophils. The severity of neutropenia is determined by the absolute neutrophil count (ANC) measured in cells per microliter of blood. Mild neutropenia ($1000 \leq ANC < 1500$); moderate neutropenia ($500 \leq ANC < 1000$); and severe neutropenia ($ANC < 500$) are common levels determined by those of ordinary skill in the art.

As used herein "prevention" of *S. aureus*-associated pneumonia in an immunocompromised mammalian subject refers to reducing the risk of an immunocompromised subject from acquiring *S. aureus*-associated pneumonia at the time of an infection event. Suitably, the risk of an immunocompromised subject acquiring *S. aureus*-associated pneumonia is reduced by at least 30% as compared to an immunocompromised that has not been administered an anti-AT antibody or antigen-binding fragment prior to the infection event. More suitably the risk is reduced by at least 40%, at least 50%, at least 60%, at least 70%, at least 80%, at least 90% or the risk is completely eliminated as compared to an immunocompromised subject that has not been administered an anti-AT antibody or antigen-binding fragment thereof prior to the infection event.

In methods for reducing the severity of *S. aureus*-associated pneumonia in a mammalian subject, such methods suitably comprise administering an effective amount of an isolated anti-*S. aureus* alpha toxin (anti-AT) antibody or antigen-binding fragment thereof to a subject that is exhibiting symptoms of *S. aureus*-associated pneumonia. Such symptoms can include, for example, cough, chest pain, fever, and difficulty breathing.

As used herein "reducing the severity" as it is used with reference to pneumonia refers to reducing the symptoms that a subject (suitably an immunocompromised subject) that has acquired *S. aureus*-associated pneumonia is exhibiting. Suitably, the symptoms are reduced by at least 30% as compared to the symptoms that a subject that also has acquired *S. aureus*-associated pneumonia is exhibiting, but the subject has not been administered an anti-AT antibody or antigen-binding fragment thereof. More suitably the symptoms are reduced by at least 40%, at least 50%, at least 60%, at least 70%, at least 80%, at least 90% or the symptoms are completely eliminated (i.e., the subject is cured of the infection and therefore pneumonia) as compared to an immunocompromised subject that has not been administered an anti-AT antibody or antigen-binding fragment thereof prior to the infection event.

As described herein, suitably the various methods are carried out on mammalian subject that are humans, including adults of any age and children.

Suitably, in the methods described herein, the antibodies or antigen-binding fragments thereof that are administered are isolated Fv, Fab, Fab', and F(ab')2 antigen-binding fragments. In further embodiments, the antibody is a full-length antibody, as described herein. Suitably the antibody comprises an Fc variant region as described in detail throughout.

The methods described throughout suitably utilize isolated antibodies or antigen-binding fragments thereof that immunospecifically bind to a *Staphylococcus aureus* alpha toxin polypeptide. Such antibodies and antigen-binding fragments thereof suitably comprise:

(a) a VH CDR1 comprising the amino acid sequence of SEQ ID NO: 7, 10, 13 or 69;
(b) a VH CDR2 comprising the amino acid sequence of SEQ ID NO: 8, 11, 14, 17, 70 or 75;
(c) a VH CDR3 comprising the amino acid sequence of SEQ ID NO: 9, 12, 15, 18, 16, 65, 66, 67, 71, 72, 76 or 78;
(d) a VL CDR1 comprising the amino acid sequence of SEQ ID NO: 1 or 4;
(e) a VL CDR2 comprising the amino acid sequence of SEQ ID NO: 2, 5, 73 or 77; and
(f) a VL CDR3 comprising the amino acid sequence of SEQ ID NO: 3, 6, 64, 68 or 74.

In addition, mutants, variants and derivatives of such antibodies or antigen-binding fragments can also be utilized, as well as antibodies or antigen-binding fragments thereof exhibiting at least 90% identity to the recited amino acid sequences.

In further embodiments, the various methods described herein utilize antibodies or antigen-binding fragments thereof comprising CDRs including, for example, VH CDR1, VH CDR2, VH CDR3, VL CDR1, VL CDR2 and VL CDR3 corresponding to the amino acid sequences of SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74

In embodiments, the isolated anti-AT antibody or antigen-binding fragment thereof utilized in the various methods described herein comprises a heavy chain variable domain having at least 90% identity to the amino acid sequence of SEQ ID NO: 20, 22, 24, 26, 28, 41, 43, 45, 47, 49, 51, 53, 55, 57, 79, 59, 61, or 62 and comprises a light chain variable domain having at least 90% identity to the amino acid sequence of SEQ ID NO: 19, 21, 23, 25, 27, 42, 44, 46, 48, 50, 52, 54, 56, 58, 60 or 63.

In still further embodiments of the methods described herein, the isolated anti-AT antibody or antigen-binding fragment thereof utilized comprises a heavy chain variable domain of SEQ ID NO 20, 22, 24, 26, 28, 41, 43, 45, 47, 49, 51, 53, 55, 57, 79, 59, 61, or 62 and a light chain variable domain of SEQ ID NO: 19, 21, 23, 25, 27, 42, 44, 46, 48, 50, 52, 54, 56, 58, 60 or 63.

In additional embodiments, the methods described herein utilize anti-AT antibodies or antigen-binding fragments thereof have VH and VL corresponding to the amino acid sequences of SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

In suitable embodiments, the isolated anti-AT antibody comprises an isolated anti-AT antibody having an Fc variant domain, wherein the antibody comprises a VH-IgG1-YTE corresponding to SEQ ID NO: 80 and/or a VL-Kappa corresponding to SEQ ID NO: 81.

EXAMPLES

Example 1: Establishment of Sepsis Model

Preparation of Bacteria Challenge Dose

*S. aureus* SF8300 (USA300) was provided by Binh Diep (University California San Francisco). Bacteria were cultured overnight at 37° C. in 50 mL of tryptic soy broth (TSB) shaking at 250 rpm. Ten mL from the overnight culture were added to 1 L of fresh TSB and the bacteria grown at 37° C. with shaking to an optical density at 600 nm (OD600) of 0.8. Bacteria were recovered by centrifugation at 8000 rpm for 15 min at 4° C. and washed in phosphate buffer saline (PBS).

The bacteria were collected by centrifugation and resuspended in PBS with 10% glycerol to a final bacterial stock concentration of ~$2\times10^{10}$ cfu/mL.

Mouse Challenge and Survival

Groups of ten 8-9 week old female BALB/c mice were injected intra-peritoneally (IP) with LC10 at indicated concentrations or R347 (45 mg/kg) mAbs in 500 µL PBS. Animals were then challenged intravenously (IV) in the tail vein 24 h later with 200 µL of a bacterial suspension ($5\times10^7$ cfu diluted in PBS, pH 7.2, from frozen stock). Mice were monitored for survival for 14 days post challenge. Statistical analysis was assessed with a logrank test: R347 (control) versus LC10 (anti-AT Ab) immunized animals.

Bacterial Load in Heart

Infected mice were euthanized with $CO_2$ 14 h post infection. The heart was removed, homogenized in lysing matrix A tubes in 1 mL cold PBS, and plated on TSA plates for bacterial enumeration. The bacterial load in heart tissue was analyzed in pairwise comparison between R347 and LC10 mAbs with an unpaired two-tailed Student's t-test. Data were considered significant if $p<0.05$.

Bacteria Load in Blood

Animals were euthanized with $CO_2$ at 8, 24, 48, 72, and 144 h post infection. Blood was collected by cardiac puncture, and 100 µL was plated immediately on a TSB plate for cfu enumeration. Data were analyzed with an unpaired student t test. Values were considered statistically different between LC10 and R347 mAbs if $p<0.05$.

Example 2: Prophylactic Effect of Anti-AT Antibodies in Sepsis

To determine if anti-AT antibody mediated inhibition of AT would affect the progression of sepsis, groups of 10 mice were passively immunized with LC10 (45 and 15 mg/kg) or an isotype control (R347, 45 mg/kg) 24-h prior to IV challenge with *S. aureus* SF8300 (USA300), and survival monitored for 14 days. LC10 prophylaxis significantly increased survival, indicating AT plays a key role in systemic *S. aureus* disease and its inhibition with LC10 protects animals from death (FIG. 1).

One hallmark of *S. aureus* sepsis is bacterial agglutination and thromboembolic lesion formation which is measured as bacterial CFU in the heart (McAdow et al, 2011). To determine if LC10 prophylaxis reduced the bacterial load in the heart, mice were passively immunized with LC10 (15 and 45 mg/kg) or R347 (45 mg/kg) 24 h prior to IV infection with SF8300. Fourteen-hours post infection the animals were euthanized and their hearts processed for CFU enumeration. Mice passively immunized with LC10 exhibited a significant reduction in heart CFU relative to mice that received the R347 control (FIG. 2).

The effect of LC10 prophylaxis on bacterial counts in the blood was also assessed 24 to 72 h post IV infection. Bacterial counts in the bloodstream of the infected mice remained at ~$10^3$ cfu for the R347 treated mice through 72 h. However, LC10 prophylaxis resulted in reduced bacterial load at all time points tested with a maximal reduction of 2 orders of magnitude at 72 h (FIG. 3). These results indicate that AT is important to the progression of sepsis, and inhibition of AT with LC10 reduces bacterial cfu in the bloodstream and heart and promotes survival following IV challenge with a lethal dose of *S. aureus*.

Example 3: Establishment of an Immunocompromised Pneumonia Model

Immunocompromised individuals, particularly those suffering from neutropenia, are at increased risk for *S. aureus* infections (Andrews and Sullivan, 2003; Bouma et. al., 2010). To study the effectiveness of anti-AT antibodies for use in the prevention of *S. aureus* pneumonia in immunocompromised individuals, an immunocompromised murine pneumonia model was developed and utilized. To mimic infection in an immunocompromised population of individuals, mice were rendered neutropenic through the administration of cyclophosphamide, an alkylating agent known to deplete white blood cells in mice including neutrophils, lymphocytes and platelets (Zuluaga, et. al. 2006).

Experiments were conducted to determine the optimal cyclophosphamide (CPM) dosing regimen necessary to reduce circulating immune cells in C57BL/6 mice by >90%. CPM powder was dissolved in sterile water for injection to a final concentration of 20 mg/mL. Groups of 20 mice were treated by intraperitoneal injection on Days 0 and 3 with different CPM dosing regimens. Groups of 5 animals were sacrificed on Days 0, 1, 4 and 6 and blood was collected by cardiac puncture into Vacutainer EDTA tubes. Differential white blood cell (WBC) counts (neutrophils, lymphocytes) were then obtained using a Sysmex automated hematology analyzer.

Mouse Pneumonia Model

Preparation of Bacteria Challenge Dose

*S. aureus* SF8300 was cultured overnight at 37° C. in 50 mL tryptic soy broth (TSB) shaking at 250 rpm. Ten mL overnight culture was added to 1 L fresh TSB, and the bacteria were grown at 37° C. with shaking to an optical density of 0.8 at 600 nm (OD600). Bacteria were recovered by centrifugation at 8000 rpm for 15 min at 4° C. and washed in phosphate buffer saline (PBS). The bacteria were collected again by centrifugation and resuspended in PBS with 10% glycerol to a final bacteria stock concentration of $2\times10^{10}$ CFU/mL.

Immunocompromised Mouse Pneumonia Model

Initially, the minimum lethal *S. aureus* dose in immunocompromised mice was identified in a challenge dose titration experiment. Twenty-four hours after the second CPM dose, the immunocompromised mice were anesthetized with isofluorane before inoculation with 50 µL of a *S. aureus* suspension ($1\times10^7$ to $2\times10^8$ CFU) into the left and right nares. Animals were placed into a cage in a supine position for recovery and observed for lethality over a 7-day period.

Example 4: Prophylactic Effect of Anti-Staph AT Antibodies in Neutropenic Pneumonia Anti-AT mAb Efficacy Study in Immunocompromised Pneumonia Model There were 30 animals used in this experiment, randomly assigned into 3 groups. The animals were administered CPM 4 days and 1 day prior to infection. Each group was also administered either LC10 (45 or 15 mg/kg) or R347 (45 mg/kg) 24 hr prior (Day −1) to intranasal (IN) challenge with *S. aureus* SF8300 ($5\times10^7$), and survival was observed for up to 7 days. Statistical significance was determined using a Log-rank test.

Verification of Immunodeficiency

Experiments were conducted to determine the optimal CPM dose regimen to reduce the total WBC count, including neutrophils, by 90%. Groups of 20 mice were treated with 6 different CPM dosing regimens on Days 0 and 3. Blood samples from 5 mice in each dose group were collected on Days 0, 1, 4, and 6, and total and differential WBC counts were performed using a Sysmex hematology analyzer. On Days 4 and 6 the animals in Group 6 (1st CPM dose 150 mg/kg; 2nd CPM dose 100 mg/kg [CPM150/100] exhibited a 90% reduction in total WBC relative to untreated animals. There was a 90% reduction in neutrophils and lymphocytes on Day 4 and day 6 in this group (FIG. 4). Leukocytes began to recover at Day 7. These results are consistent with those reported previously (Zuluaga et al., 2006). Therefore, a CPM 150/100 dose was selected to evaluate LC10 prophylaxis in immunocompromised animals.

Determination of Bacterial Challenge Dose in Immunocompromised Pneumonia Model

To determine the minimum lethal challenge dose in immunocompromised animals, S. aureus SF8300 was titrated (from $2 \times 10^8$ to $1 \times 10^7$ CFU) by IN challenge in groups of 5 mice. Lethality was observed for 7 days (FIG. 5). The lowest lethal dose was $5 \times 10^7$ CFU and was selected as the dose to test LC10 prophylaxis.

LC10 Increases Survival in Immunocompromised Pneumonia Animals

To understand the effect of LC10 prophylaxis in immunocompromised mice, CPM-injected animals were administered LC10 (45 or 15 mg/kg) or R347 at 45 mg/kg 24 hours prior to IN challenge with 50 µL of a bacterial suspension (SF8300 at $5 \times 10^7$ CFU) and lethality was observed as describe above.

Passive immunization with LC10 at 45 or 15 mg/kg resulted in a significant increase in survival relative to the R347 control (p<0.0001) (FIG. 6). To confirm animals were immunocompromised in this study, blood samples were collected from groups of 5 uninfected mice on Days −4, −3, 1, 0, 2, and 3. Total and differential WBC counts were performed, and there was a 90% reduction in total WBC, as well as neutrophils and lymphocytes, between days −4 and −2 for these animals. The animals exhibited severe neutropenia (≤10 neutrophils/µL blood) on Days 0-2 (FIG. 7). Therefore, prophylaxis with LC10 can reduce disease severity in a S. aureus neutropenic mouse pneumonia model.

CONCLUSIONS

An S. aureus immunocompromised mouse pneumonia model was developed using cyclophosphamide resulting in >90% reduction in circulating white blood cells including neutrophils and lymphocytes. The mice exhibited severe neutropenia with ≤10 neutrophils/µL blood. Prophylaxis with LC10 significantly improved survival in a S. aureus neutropenic mouse pneumonia model. These results indicate that passive immunization with LC10 24 hours prior to S. aureus infection of mice rendered neutropenic by the administration of cyclophosphamide significantly improves survival. Thus, this demonstrates that anti-AT antibodies can prevent disease in immunocompromised patients.

All documents, patents, journal articles and other materials cited in the present application are hereby incorporated by reference.

Although the present invention has been fully described in conjunction with several embodiments thereof with reference to the accompanying drawings, it is to be understood that various changes and modifications can be apparent to those skilled in the art. Such changes and modifications are to be understood as included within the scope of the present invention as defined by the appended claims, unless they depart there from.

What is claimed is:

1. A method of preventing or reducing the severity of *Staphylococcus aureus*-associated (*S. aureus*-associated) pneumonia in an immunocompromised mammalian subject, comprising administering to said subject an effective amount of an isolated anti-*S. aureus* alpha toxin (anti-AT) antibody or antigen-binding fragment thereof, wherein the isolated antibody or antigen-binding fragment thereof immunospecifically binds to a *S. aureus* alpha toxin polypeptide and includes:
   (a) a VH CDR1 comprising the amino acid sequence of SEQ ID NO: 69;
   (b) a VH CDR2 comprising the amino acid sequence of SEQ ID NO: 70;
   (c) a VH CDR3 comprising the amino acid sequence of SEQ ID NO: 71;
   (d) a VL CDR1 comprising the amino acid sequence of SEQ ID NO: 1;
   (e) a VL CDR2 comprising the amino acid sequence of SEQ ID NO: 2; and
   (f) a VL CDR3 comprising the amino acid sequence of SEQ ID NO: 68.

2. The method of claim 1, wherein the isolated antibody or antigen-binding fragment thereof comprises a heavy chain variable domain of SEQ ID NO: 57.

3. The method of claim 1, wherein the isolated antibody or antigen-binding fragment thereof comprises a light chain variable domain of SEQ ID NO: 58.

4. The method of claim 1, wherein the isolated antibody or antigen-binding fragment thereof comprises a heavy chain variable domain of SEQ ID NO: 57 and a light chain variable domain of SEQ ID NO: 58.

5. The method of claim 1, wherein the isolated antibody or antigen-binding fragment thereof comprises a heavy chain of SEQ ID NO: 80.

6. The method of claim 3, wherein the isolated antibody or antigen-binding fragment thereof comprises a heavy chain of SEQ ID NO: 80.

7. The method of claim 1, wherein the isolated antibody or antigen-binding fragment thereof comprises a light chain of SEQ ID NO: 81.

8. The method of claim 2, wherein the isolated antibody or antigen-binding fragment thereof comprises a light chain of SEQ ID NO: 81.

9. The method of claim 1, wherein the isolated antibody or antigen-binding fragment thereof comprises a heavy chain of SEQ ID NO: 80 and a light chain of SEQ ID NO: 81.

10. The method of claim 1, wherein said immunocompromised mammalian subject is human.

11. The method of claim 4, wherein said immunocompromised mammalian subject is human.

12. The method of claim 9, wherein said immunocompromised mammalian subject is human.

13. The method of claim 1, wherein said isolated antibody or antigen-binding fragment thereof is selected from the group consisting of Fv, Fab, Fab', and F(ab')2.

14. The method of claim 1, wherein said antibody is a full-length antibody.

15. The method of claim 14, wherein said antibody comprises an Fc variant region.

16. The method of claim 1, wherein the administering is through intravenous (IV) administration.

17. The method of claim 4, wherein the administering is through intravenous (IV) administration.

18. The method of claim 9, wherein the administering is through intravenous (IV) administration.

19. The method of claim 10, wherein the administering is through intravenous (IV) administration.

20. The method of claim 11, wherein the administering is through intravenous (IV) administration.

21. The method of claim 12, wherein the administering is through intravenous (IV) administration.

* * * * *

SEQUENCE LISTING

```
<160> NUMBER OF SEQ ID NOS: 82

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Ser Ile Ser Ser Trp Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Ser Ser Leu Glu Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Gln Gln Tyr Asn Ser Tyr Trp Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Arg Asn Asp Leu Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Asp Tyr Asn Tyr Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Tyr Asp Met His
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Gly Thr Ala Gly Asp Thr Tyr Tyr Pro Gly Ser Val Lys Gly
1               5                   10                  15

<210> SEQ ID NO 9
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Asp Asn Tyr Ser Ser Thr Gly Gly Tyr Tyr Gly Met Asp Val
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Tyr Asp Met His
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Gly Thr Asp Gly Asp Thr Tyr Tyr Pro Gly Ser Val Lys Gly
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Tyr Ser Ser Ser Asn His Tyr Asn Gly Met Asp Val
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Ala Met Thr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ile Ser Gly Ser Gly Gly Ser Thr Tyr Tyr Ala Asp Ser Val Lys
1               5                   10                  15
```

Gly

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Gly Arg Gln Val Glu Asp Tyr Tyr Tyr Tyr Gly Met Asp Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Tyr Ser Pro Thr Gly His Tyr Met Gly Met Asp Val
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Ile Asp Thr Ala Gly Asp Thr Tyr Tyr Pro Gly Ser Val Lys Gly
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Arg Tyr Ser Gly Asn Phe His Tyr Asn Gly Met Asp Val
1               5                   10

<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly

```
                     50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                     85                  90                  95

Phe Gly Gln Gly Thr Lys Val Glu Ile Lys
                100                 105

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
 65                  70                  75                  80

Gln Leu Asn Ser Leu Arg Ala Gly Asp Thr Ala Val Tyr Phe Cys Ala
                85                  90                  95

Arg Asp Asn Tyr Ser Ser Thr Gly Gly Tyr Tyr Gly Met Asp Val Trp
                100                 105                 110

Gly Gln Gly Thr Thr Val Thr Val Ser Ser
            115                 120

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
                100                 105
```

```
<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
    50                  55                  60

Gly Arg Phe Ile Ile Ser Arg Glu Asn Ala Lys Asn Ser Leu Tyr Leu
65                  70                  75                  80

Glu Met Asn Ser Leu Arg Ala Gly Asp Thr Ala Val Tyr Tyr Cys Ala
                85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
        115                 120

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 24
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
 50                  55                  60

Gly Arg Phe Ile Ile Ser Arg Glu Asn Ala Lys Asn Ser Leu Tyr Leu
 65                  70                  75                  80

Glu Met Asn Ser Leu Arg Ala Gly Asp Thr Ala Val Tyr Tyr Cys Ala
                85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
            115                 120

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
 50                  55                  60

Lys Gly Arg Phe Thr Val Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Asp Gly Arg Gln Val Glu Asp Tyr Tyr Tyr Tyr Gly Met
            100                 105                 110

Asp Val Trp Gly Gln Gly Thr Thr Val Thr Val Ser Ser
        115                 120                 125

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Val Ile Asp Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Asp Arg Tyr Ser Gly Asn Phe His Tyr Asn Gly Met Asp Val Trp
            100                 105                 110

Gly Gln Gly Thr Thr Val Thr Val Ser Ser
        115                 120

<210> SEQ ID NO 29
```

<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaaactcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attggacgtt cggccaaggg     300
accaaggtgg aaatcaaa                                                   318

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaggtgcagc tggtggagtc tgggggaggc ttggtacagc ctggggggtc cctgagactc      60
tcctgtgcag cctctggatt caccttcagt agctacgaca tgcactgggt ccgccaagct     120
acaggaaaag gtctggagtg gtctcaggt attggcactg ctggtgacac atattatcca     180
ggctccgtga agggccgatt caccatctcc agagaaaatg ccaagaactc cttgtatctt     240
caattgaaca gcctgagagc cggggacacg gctgtgtact ctgtgcaag agacaattat     300 agcagcaccg gggggtacta cggtatggac gtctggggcc aagggaccac ggtcaccgtc     360
tcctca                                                               366

<210> SEQ ID NO 31
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaaactcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attggacgtt cggccaaggg     300
accaaggtgg aaatcaaa                                                   318

<210> SEQ ID NO 32
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gaggtgcagc tggtggagtc tggggggaggc ttggtacagc ctggggggtc cctgagactc        60
tcctgtgcag cctctggatt caccttcagt aggtacgaca tgcactgggt ccgccaagct       120
acaggaaaag gtctggagtg gtctcagtt attggtactg atggtgacac atactatcca       180
ggctccgtga agggccgatt catcatctcc agagaaaatg ccaagaactc cttgtatctt       240
gaaatgaaca gcctgagagc cggggacacg gctgtgtatt actgtgcaag agatcggtat       300
agcagctcga accactacaa cggtatggac gtctggggcc aagggaccac ggtcaccgtc       360
tcctca                                                                  366
```

<210> SEQ ID NO 33
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gacatccaga tgacccagtc tccttccacc ctgtctgcat ctgtaggaga cagagtcacc        60
atcacttgcc gggccagtca gagtattagt agctggttgg cctggtatca gcagaaacca       120
gggaaagccc ctaaggtcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagtt attggacgtt cggccaaggg       300
accaaggtgg aaatcaaa                                                     318
```

<210> SEQ ID NO 34
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
gaggtgcagc tggtggagtc tggggggaggc ttggtacagc ctggggggtc cctgagactc        60
tcctgtgcag cctctggatt caccttcagt aggtacgaca tgcactgggt ccgccaagct       120
acaggaaaag gtctggagtg gtctcagtt attggtactg atggtgacac atactatcca       180
ggctccgtga agggccgatt catcatctcc agagaaaatg ccaagaactc cttgtatctt       240
gaaatgaaca gcctgagagc cggggacacg gctgtgtatt actgtgcaag agatcggtat       300
agcagctcga accactacaa cggtatggac gtctggggcc aagggaccac ggtcaccgtc       360
tcctca                                                                  366
```

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gccatccaga tgacccagtc tccatcctcc ctgtctgcat ctgtaggaga cagagtcacc        60
atcacttgcc gggcaagtca gggcattaga aatgatttag gctggtatca gcagaaacca       120
gggaaagccc ctaagctcct gatctatgat gcatccagtt tacaaagtgg ggtcccatca       180
```
aggttcagcg gcagtggatc tggcacagat tcactctca ccatcagcag cctgcagcct    240
gaagattttg caacttatta ctgtctacaa gattacaatt acccgtggac gttcggccaa    300
gggaccaagg tggaaatcaa a                                              321

<210> SEQ ID NO 36
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gaggtgcagc tgttggagtc tgggggaggc ttggtacagc ctggggggtc cctgagactc     60
tcctgtgcag cctctggatt cacctttagc agctatgcca tgacctgggt ccgccaggct    120
ccagggaagg ggctggaatg ggtctcagtt attagtggta gtggtggtag cacatactac    180
gcagactccg tgaagggccg gttcaccgtc tccagagaca attccaagaa cacgctgtat    240
ctgcaaatga acagcctgag agccgaggac acggccgtat attactgtgc gaaagatggg    300
aggcaggtcg aggattacta ctactactac ggtatggacg tctggggcca agggaccacg    360
gtcaccgtct cctca                                                    375

<210> SEQ ID NO 37
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attggacgtt cggccaaggg    300
accaaggtgg aaatcaaa                                                 318

<210> SEQ ID NO 38
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gaggtgcagc tggtggagtc tgggggaggc ttggtacagc ctggggggtc cctgagactc     60
tcctgtacag cctctggatt caccttcagt agttacgaca tgcactgggt ccgccaagct    120
acaggaaaag gtctggagtg ggtctcagtt attgatactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgtaag agataggtat    300
agtgggaact ccactacaa cggtatggac gtctggggcc aagggaccac ggtcaccgtc    360
tcctca                                                              366

<210> SEQ ID NO 39
<211> LENGTH: 293
<212> TYPE: PRT
<213> ORGANISM: Staphylococcus aureus

<400> SEQUENCE: 39

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 40
<211> LENGTH: 293
<212> TYPE: PRT
<213> ORGANISM: Staphylococcus aureus

<400> SEQUENCE: 40

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30
```

```
Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
```

```
            85                  90                  95
Arg Asp Arg Tyr Ser Pro Thr Gly His Tyr Met Gly Met Asp Val Trp
        100                 105                 110
Gly Gln Gly Thr Thr Val Thr Val Ser Ser
        115                 120

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asp Thr Tyr Trp Thr
                85                  90                  95
Phe Gly Gln Gly Thr Lys Val Glu Ile Lys
        100                 105

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Thr Gly Lys Gly Leu Glu Trp Val
        35                  40                  45
Ser Gly Ile Gly Thr Ala Gly Asp Thr Tyr Tyr Pro Gly Ser Val Lys
    50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
Arg Asp Arg Tyr Ser Arg Thr Gly His Tyr Met Gly Met Asp Val Trp
        100                 105                 110
Gly Gln Gly Thr Thr Val Thr Val Ser Ser
        115                 120

<210> SEQ ID NO 44
<211> LENGTH: 106
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Arg Thr His Tyr Met Gly Met Ser Leu Trp
            100                 105                 110

Gly Gln Gly Thr Thr Val Thr Val Ser Ser
        115                 120

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105
```

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
            115                 120
```

<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95
```

Phe Gly Gln Gly Thr Lys Val Glu Ile Lys
            100                 105

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Met Gly Met Ser Leu Trp
            100                 105                 110

Gly Gln Gly Thr Thr Val Thr Val Ser Ser
        115                 120

<210> SEQ ID NO 52
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 53
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Asp Arg Tyr Ser Arg Thr Gly His Tyr Met Gly Met Asp Val Trp
        100                 105                 110

Gly Gln Gly Thr Thr Val Thr Val Ser Ser
        115                 120

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
            85                  90                  95

Phe Gly Gln Gly Thr Lys Val Glu Ile Lys
        100                 105

<210> SEQ ID NO 55
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Asp Asn Tyr Ser Ser Thr Gly Gly Tyr Tyr Gly Met Asp Val Trp
        100                 105                 110

Gly Gln Gly Thr Thr Val Thr Val Ser Ser
        115                 120

<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 57
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Pro Thr Gly Gly Tyr Tyr Gly Met Asp Val Trp
            100                 105                 110

Gly Gln Gly Thr Thr Val Thr Val Ser Ser
        115                 120

<210> SEQ ID NO 60
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Lys Ser Gly Val Pro Ser Arg Phe Ser Gly

```
            50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Ser Tyr Trp Thr
                 85                  90                  95

Phe Gly Gln Gly Thr Lys Val Glu Ile Lys
            100                 105

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
             20                  25                  30

Asp Met His Trp Val Arg Gln Ala Thr Gly Lys Gly Leu Glu Trp Val
         35                  40                  45

Ser Gly Ile Gly Thr Arg Gly Asp Thr Tyr Tyr Pro Asp Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
            115                 120

<210> SEQ ID NO 62
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
             20                  25                  30

Asp Met His Trp Val Arg Gln Ala Thr Gly Lys Gly Leu Glu Trp Val
         35                  40                  45

Ser Gly Ile Gly Thr Arg Gly Asp Thr Tyr Tyr Pro Asp Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Lys Tyr Ser Pro Thr Gly His Tyr Tyr Gly Met Asp Val Trp
            100                 105                 110

Gly Gln Gly Thr Thr Val Thr Val Ser Ser
```

```
                  115                 120
```

<210> SEQ ID NO 63
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Val Lys Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Trp Thr
                85                  90                  95

Phe Gly Gln Gly Thr Lys Val Glu Ile Lys
            100                 105
```

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gln Gln Tyr Asp Thr Tyr Trp Thr
1               5
```

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Asp Arg Tyr Ser Arg Thr Gly His Tyr Met Gly Met Asp Val
1               5                   10
```

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Asp Arg Tyr Ser Arg Thr Gly His Tyr Met Gly Met Ser Leu
1               5                   10
```

<210> SEQ ID NO 67
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Asn Tyr Ser Arg Thr Gly His Tyr Met Gly Met Asp Val
1               5                   10

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gln Tyr Ala Asp Tyr Trp Thr
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser His Asp Met His
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ile Gly Thr Ala Gly Asp Thr Tyr Tyr Pro Asp Ser Val Lys Gly
1               5                   10                  15

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Arg Tyr Ser Pro Thr Gly His Tyr Tyr Gly Met Asp Val
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Asn Tyr Ser Pro Thr Gly Gly Tyr Tyr Gly Met Asp Val
```

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Ala Ser Ser Leu Lys Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Glu Ser Tyr Trp Thr
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ile Gly Thr Arg Gly Asp Thr Tyr Tyr Pro Asp Ser Val Lys Gly
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Lys Tyr Ser Pro Thr Gly His Tyr Tyr Gly Met Asp Val
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ala Ser Ser Leu Val Lys
1               5

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 78

Asp Arg Tyr Ser Pro Thr Gly His Tyr Met Gly Met Ser Leu
1               5                   10

<210> SEQ ID NO 79
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
                20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Asp Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 80
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
                20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Asp Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Tyr Ile Thr Arg Glu Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 81
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile

```
                    35                  40                  45
Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu
    210

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Val Ile Asp Thr Ala Gly Asp Thr Tyr Tyr Pro Gly Ser Val Lys
1               5                   10                  15

Gly
```